US010087194B2

(12) United States Patent
Yang

(10) Patent No.: US 10,087,194 B2
(45) Date of Patent: Oct. 2, 2018

(54) PODOPHYLLOTOXIN DERIVATIVES AND THEIR USE

(71) Applicants: California Pacific Medical Center, San Francisco, CA (US); Catholic Healthcare West, San Francisco, CA (US)

(72) Inventor: Li-Xi Yang, San Francisco, CA (US)

(73) Assignees: California Pacific Medical Center, San Francisco, CA (US); Catholic Healthcare West, San Francisco, CA (US)

( * ) Notice: Subject to any disclaimer, the term of this patent is extended or adjusted under 35 U.S.C. 154(b) by 0 days.

(21) Appl. No.: 14/924,526

(22) Filed: Oct. 27, 2015

(65) Prior Publication Data

US 2017/0114076 A1    Apr. 27, 2017

(51) Int. Cl.

| C07H 17/04 | (2006.01) |
| C07D 491/22 | (2006.01) |
| C07D 519/00 | (2006.01) |
| A61K 9/00 | (2006.01) |
| A61K 9/127 | (2006.01) |
| C07D 493/04 | (2006.01) |

(52) U.S. Cl.
CPC .......... *C07D 519/00* (2013.01); *A61K 9/0019* (2013.01); *A61K 9/1271* (2013.01); *C07D 491/22* (2013.01); *C07D 493/04* (2013.01); *C07H 17/04* (2013.01)

(58) Field of Classification Search
USPC ...................................................... 536/18.1
See application file for complete search history.

(56) References Cited

U.S. PATENT DOCUMENTS

| 2,530,037 A | 11/1950 | Willis |
| 3,524,844 A | 8/1970 | Keller-Juslen et al. |
| 4,965,348 A | 10/1990 | Saulnier et al. |
| 5,534,499 A | 7/1996 | Ansell |
| 5,614,549 A | 3/1997 | Greenwald et al. |
| 5,840,900 A | 11/1998 | Greenwald et al. |
| 5,880,131 A | 3/1999 | Greenwald et al. |
| 6,096,336 A | 8/2000 | Cao et al. |
| 6,121,451 A * | 9/2000 | Henegar ............... C07D 213/61 546/116 |
| 6,251,382 B1 | 6/2001 | Greenwald et al. |
| 6,566,393 B1 | 5/2003 | Lee et al. |
| 7,342,114 B2 | 3/2008 | Yang |
| 7,605,262 B2 | 10/2009 | Yang |
| 8,158,809 B2 | 4/2012 | Yang |
| 2009/0298870 A1 | 12/2009 | Yang |
| 2011/0184009 A1 | 7/2011 | Yang |
| 2014/0219914 A1 | 8/2014 | Govindan et al. |

FOREIGN PATENT DOCUMENTS

| FR | 2837824 A1 | 3/2002 |
| GB | 1 114 123 | 5/1968 |
| JP | 01-117885 | 5/1989 |
| JP | 02-300124 | 2/1990 |
| WO | WO-96/23794 A | 8/1996 |
| WO | WO-98/07713 A | 2/1998 |
| WO | WO-00/01417 | 1/2000 |
| WO | WO-00/29427 A | 5/2000 |
| WO | WO-02/26220 | 4/2002 |
| WO | WO-02/102804 | 12/2002 |
| WO | WO-02/102805 | 12/2002 |
| WO | WO-03/082875 A | 10/2003 |

OTHER PUBLICATIONS

Denny, W., "Prodrug Strategies in Cancer Therapy", European Journal of Medicinal Chemistry, 36, 2001, pp. 577-595.*
Brodin, et al. "In vitro release studies on lidocaine aqueous solutions, micellar solutions, and o/w emulsions". Acta Pharm Suec. 19: 267-284 (1982).
Cho et al., Antitumor Agents. 163. Three-dimensional quantitative structure-activity relationship study of 4'-O-demethylepipodophyllotoxin analogs using the modified CoMFA/q2-GRS approach, Journal of Medicinal Chemistry (1996), 39(7), 1383-95, CODEN: JMCMAR; ISSN: 0022-2623, American Chemical Society, School of Pharmacy, University of North Carolina, US.
Communication pursuant to Article 94(3) EPC in Application No. 04777395.7-1462 dated Aug. 4, 2015.
Communication pursuant to Article 94(3) EPC in Application No. 04777395.7-1462 dated Jul. 29, 2014.
Fischer et al. "Preparation of peptide derivatives for improved delivery of drug therapeutic agents". Abstract, CA 132:93654 (2000).
Forssen et al. "Selective in Vivo Localization of Daunorubicin Small Unilamellar Vesicle in Solid Tumors". Cancer Res, 52: 3255-3261 (1992).
Fung et al. "Perfluorochemical Emulsions with Fluorinated Surfactants and Anticancer Drugs". Biomater. Artif. Cells. Artif. Organs 16(1-3): 439-440 (1988).
Gan et al., "Inhibition of tumor necrosis factor-alpha (TNF-a) and interleukin-1 beta (IL-ß) secretion but not IL-6 from activated human peripheral blood monocytes by a new synthetic demethylpodophyllotoxin derivative," Journal of Cllnical Immunology (1994), 14(5), 280-8, CODEN: JCIMDO; ISSN: 0271-9142, UCLA School Medicine, University California, US.
Gan et al., "Selective inhibition of TNF-alpha and IL-1-beta synthesis and secretion from activated human monocytes by a new synthetic demethylpodophyllotoxin derivative," European Cytokine Network, (1994), vol. 5, No. 2, pp. 207; Meeting Info.: 5th International Congress on Tumor Mecrosis Factor, California, US, ISSN: 1148-5493.
Gensler et al. "Nonenolizable Podophyllotoxin Derivates". J. Med. Chem. 20(5): 635-644 (1977).
Greenwald et al. "Drug delivery of anticancer agents: water soluble 4-polyethylene glycol derivatives of the lignan, podophyllotoxin." Abstract, CA 132:15517 (1999).
Greenwald et al. "Camptothecin-20-PEG Ester Transport Forms: the Effect of Space Groups on Antitumor Activity." Bioorganic & Medicinal Chemistry, vol. 6, Jan. 1, 1998 (Jan. 1, 1998), pp. 551-562.
Gupta, R. S. et al: "Synthesis and biological activities of the C-4 esters of 4'-demethylepipodophyllotoxin" Anti-Cancer Drug Design, 2(1), 13-23 CODEN: ACDDEA; ISSN: 0266-9536, 1987.

(Continued)

*Primary Examiner* — Lezah Roberts
(74) *Attorney, Agent, or Firm* — Foley & Lardner LLP

(57) ABSTRACT

Provided herein are compounds, compositions, and methods for treating cancer in a subject in need thereof.

15 Claims, 14 Drawing Sheets

(56) References Cited

OTHER PUBLICATIONS

Hansen et at. "New Compounds Related to Podophyllotoxin and Congeners: Synthesis, Structure Elucidation and Biological Testing". Acta Chemi. Scand. 47: 1190-1200 (1993).
International Search Report and Written Opinion of the International Searching Authority from Application No. PCT/US2015/57645 dated Jan. 27, 2015, 9 pgs.
Khokhar et al. "Chemical and Biological Studies on a Series of Lipid-Soluble (trans-(R,R)- and—(S,S)-1,2-Diaminocyclohexane)platinum(II) Complexes Incorporated in Liposomes". J. Med. Chem, 34: 325-329 (1991).
Lasic. "Mixed micelles in drug delivery". Nature 335: 279-280 (1992).
Lee et al. "Anti-aids Agents. 29. Anti-HIV Activity of Modified Podophyllotoxin Derivatives". Bio & Med. Chem. Ltrs. 7(22): 2897-2902 (1997).
Lee S. Thurston et al: "Antitumor agents. 100. Inhibition of human DNA topoisomerase II by cytotoxic ether and ester derivatives of podophyllotoxin and .alpha.-peltatin", Journal of Medicinal Chemistry, vol. 32, No. 3, Mar. 1, 1989 (Mar. 1, 1989), pp. 604-608.
Leighton, Joseph et al: "Effects of a podophyllotoxin derivative on tissue culture systems in which human cancer invades normal tissue" XP002481870 retrieved from STN Database accession No. 1958:22209 & Cancer Research, 17, 336-44 CODEN: CNREA8; ISSN: 0008-5472, 1957.
Levy et al. "Antitumor agents: LXII: Synthesis and biological evaluation of podophyllotoxin esters and related derivatives". J. Pharm. Sci. 72(10): 1158-1161 (1983).
Li et al., "Reactions of podophyllotoxin with DDQ," Chinese Chemical Letters (2001), 12(12), 1057-1060, CODEN: CCLEE7; ISSN: 1101-8417, Chinese Chemical Society, Structure Research Laboratory, University of Science and Technology of China, Hefei, China.
Lie Ken Jie, M. S. F. et al: "Synthesis and spectral characteristics of some unusual fatty esters of podophyllotoxin" Chemistry and Physics of Lipids, 100(1-2), 165-170 CODEN: CPLIA4; ISSN: 0009-3084, 1999.
Mantle. "Therapeutic applications of medicinal plants in the treatment of breast cancer: a review of their pharmacology, efficacy and tolerability". PMID: 11059361 (2000).
Nagao et al. "Different mechanisms of action of long chain fatty acid esters of podophyllotoxin and esters of epipodophyllotoxin against P388 lymphocytic leukemia in mice." Medicinal Chemistry Research, 1(4): 295-9 (1991).
Nagao et al. "Preparation and testing of podophyllotoxin derivatives as neoplasm inhibitors." (Abstract) CA 112:7272 (1990).
Nagao, Yoshimitsu et al: "Different mechanisms of action of long chain fatty acid esters of podophyllotoxin and esters of epipodophyllotoxin against P388 lymphocytic leukemia in mice" XP002481871 retrieved from STN Database accession No. 1992:524013 & Medicinal Chemistry Research 1(4), 295-9 CODEN: MCREEB; ISSN: 1054-2523, 1991.

Pan et al. "Synthesis of epipodophyllotoxin carboxylates and antitumor activity in vitro". Abstract, CA 129: 175488 (1998).
Pan et al. STN Accesion No. 1998:291310; Document No. 129:175488.
Pan et al., "Synthesis and antitumor activity of new derivatives of podophyllotoxin," Current Science (1997), 72(4), 268-271, CODEN: CUSCAM; ISSN: 0011-3891, Current Science Association, Department of Chemistry, Zhejiang University, Hangzhou, China.
Pan et al., "Synthesis of epipodophyllotoxin carboxylates and antitumor activity in vitro," Yaoxue Xuebao (1997), 32(12), 898-901, CODEN: YHHPAL; ISSN: 0513-4870, Chinese Academy of Medical Sciences, Institute of Materia Media, Department of Chemistry, Zhejian University, Hangzhou, China.
Perez-Soler et al. "Anthracycline Antibodies with High Liposome Entrapment: Structural Features and Biological Activity". Cancer Res., 50:4260-4266 (1990).
Pradhan. "SN Effect of Various Drugs on the Tumor-necrotizing Activity of Several Chemical Agents in Mice". Cancer Research (1956) 1062-8.
Santangelo et al. "A convenient synthesis of phosphate esters of dopamine and epinine". Syn. Comm., 26(15): 2863-2873 (1996).
Shi et al. "Antitumor Agents 210. Synthesis and Evaluation of Taxoid-Epipodophyllotoxin Conjugates as Novel Cytotoxic Agents." Bioorganic and Medicinal Chemistry, 9(2001), 2999-3004.
Supersaxo et al. "Mixed Micelles as a Proliposomal, Lymphotropic Drug Carrier". Pharm Res. 8(10): 1280-1291 (1991).
Wang et al. "Syntheses and structure-activity relationship of podophyllotoxin derivatives as potential anticancer drugs". Abstract, CA 127:149030 (1997).
Wang Y-G et al: "New spin labeled analogs of podophyllotoxin as potential antitumor agents" Life Sciences, Pergamon Press, Oxford, GB, vol. 61, No. 5, Jan. 1, 1997 (Jan. 1, 1997), pp. 537-542.
Weller et al. "21-day oral Etoposide for metastatic breast cancer: a phase II study and review of the literature". PMID: 10857889 Am J Clin Oncol. 23(3): 258-62 (2000).
Xiao et al., "Antitumor Agents. 213. Modeling of Epipodophyllotoxin Derivatives Using Variable Section k Nearest Neighbor QSAR Method," Journal of Medicinal Chemistry (2002), 45(11), 2294-2309, CODEN: JMCMAR; ISSN: 0022-2623, American Chemical Society, Natural Products Laboratory Division of Medicinal Chemistry and Natural Products School of Pharmacy, Chapel Hill, North Carolina.
Yang et al.STN Accession No. 2002:884382 Document No. 139:159531 Abstract of Lanzhou Daxue Xuebao, Ziran Kexueban (2002), 38(2), 101-105.
Yin et al., "Synthesis and antitumor activity of 4-O-(halogenated) acyl-4'-demethylepipodophyllotoxin analogs," Yaoxue Xuebao (1993), 28(10), 758-61, CODEN: YHHPAL; ISSN: 0513-4870, Shanghai Inst. Pharm. Ind., Shanghai, China.
Yokoyama et al. "Toxicity and Antitumor Activity against Solid Tumors of Micelle-forming Polymeric Anticancer Drug and Its Extremely Long Circulation in Blood". Cancer Res. 51:3229-3236 (1991).
Yoo, Kyung Jae et al: "Immunoassay of podophyllotoxin" Journal of Natural Products, 56(5), 715-21 CODEN: JNPRDF; ISSN: 0163-3864, 1993.

* cited by examiner

PODOPHYLLOTOXIN DERIVATIVES AND THEIR USE

FIELD

The present disclosure relates to derivatives of podophyllotoxin, compositions thereof, and using them for treating various types of cancer in a subject and/or delaying or regressing various types of tumor growths in a subject.

STATE OF THE ART

Podophyllotoxin is a known compound having the formula:

The compound shows activity as an antiviral and as an antineoplastic agent. This disclosure relates to derivatives of podophyllotoxin that are useful for treating cancer.

SUMMARY

In one aspect, provided herein is a compound of formula (I):

or an N-oxide thereof, or a pharmaceutically acceptable salt of each thereof, or a pharmaceutically acceptable solvate of each of the foregoing, wherein $R^1$ is H or has a structure of:

$R^3$ is H, an optionally substituted $C_1$-$C_8$ alkyl, an optionally substituted 3-10 membered cycloalkyl, an optionally substituted 3-10 membered heterocyclyl, an optionally substituted 6-10 membered aryl, or an optionally substituted 5-10 membered heteroaryl;

$R^5$ is H or has a structure of:

and $R^{11}$ and $R^{12}$ independently is an optionally substituted $C_1$-$C_8$ alkyl.

In another aspect, provided herein is a pharmaceutical composition comprising a compound provided herein, and at least one pharmaceutically acceptable excipient.

In another aspect, provided herein is a method of treating cancer in a subject in need thereof comprising administering to the subject a therapeutically effective amount of a compound provided herein.

In another aspect, provided herein is a method of delaying or regressing tumor growth in a subject in need thereof comprising administering to the subject a therapeutically effective amount of a compound provided herein.

In another aspect, provided herein is a method of treating cancer in a subject in need thereof comprising administering to the subject a therapeutically effective amount of a pharmaceutical composition provided herein.

DETAILED DESCRIPTION

Figure 1A:
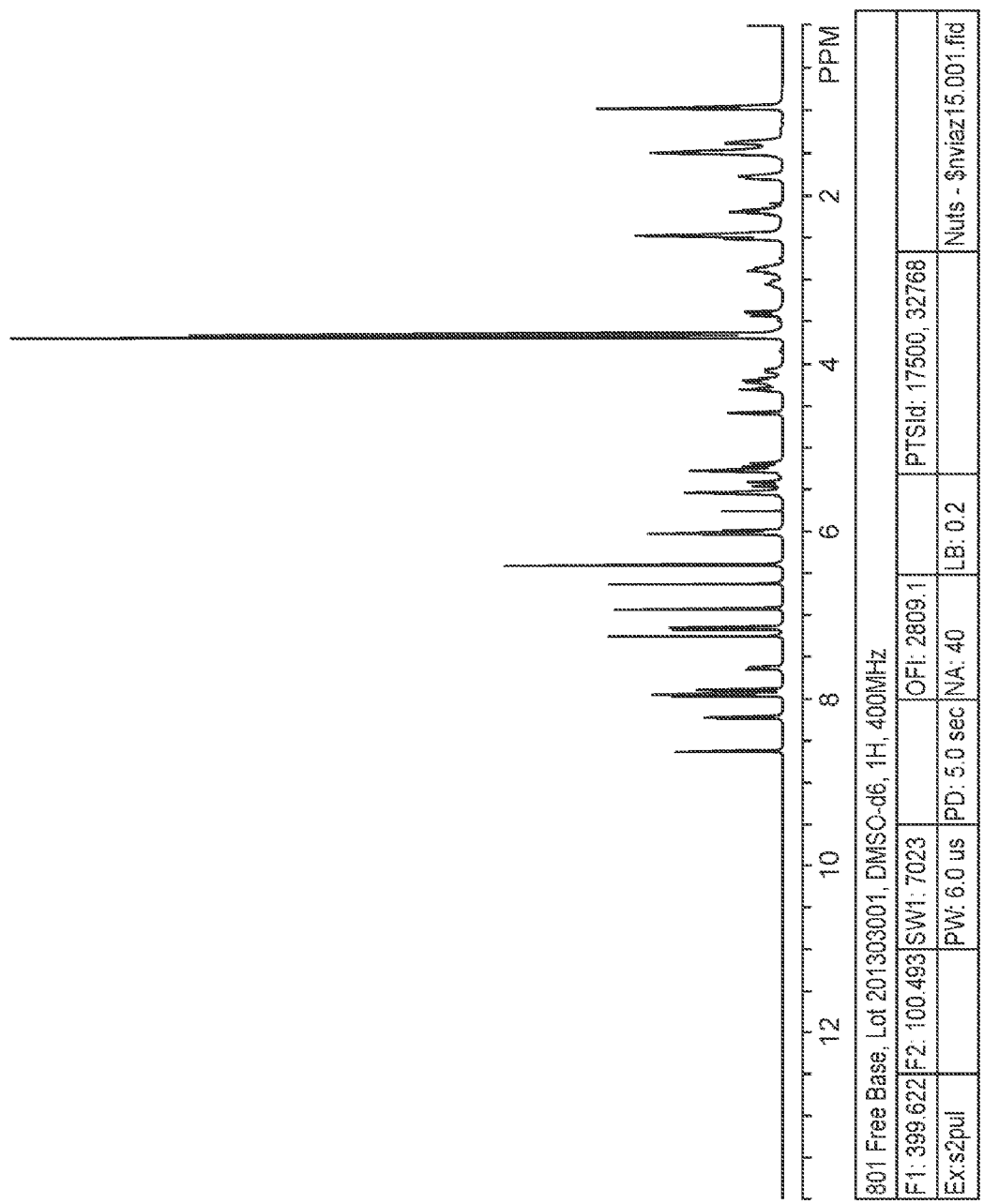
FIG. 1A shows the $^1$H Nuclear Magnetic Resonance spectra of N2.

The compounds of the disclosure are active against tumors in mice and are generally well tolerated or are contemplated to be so. They are useful for treating various types of cancer and can be formulated to prepare pharmaceutical preparations, e.g. for oral, topical, or parenteral administration.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

Throughout this disclosure, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

It must be noted that as used herein and in the appended claims, the singular forms "a", "an", and "the" include plural referents unless the context clearly dictates otherwise. Thus, for example, reference to "an excipient" includes a plurality of excipients.

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term "alkyl" refers to a monovalent, saturated aliphatic hydrocarbon radical having the indicated number of carbon atoms. For example, a "C 1-6 alkyl" or an "alkyl of 1-6 carbons" or "Alk 1-6" would refer to any alkyl group containing one to six carbons in the structure. "C 1-20 alkyl" refers to any alkyl group having one to twenty carbons. Alkyl may be a straight chain (i.e. linear) or a branched chain. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, and the like, along with branched variations thereof. The radical may be optionally substituted with substituents at positions that do not significantly interfere with the preparation of compounds falling within the scope of this invention and that do not significantly reduce the efficacy of the compounds. The alkyl may be optionally substituted with one to five substituents independently selected from the group consisting of halo, lower alkoxy, hydroxy, cyano, nitro, or amino.

The term "alkoxy" refers to a monovalent radical of the formula RO—, where R is an alkyl as defined herein. Lower alkoxy refers to an alkoxy of 1-6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The radical may be optionally substituted with one to five substituents independently selected from the group consisting of halo, lower alkyl, lower alkoxy, hydroxy, cyano, nitro, or amino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovalent radical having the formula —C(O)OH.

The term "lower alkoxycarbonyl" is a monovalent radical having the formula —C(O)OAlk, where Alk is lower alkyl.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

The term "alkylamino" is a monovalent radical having the formula —NR$_1$,R$_2$ where R$_1$ is alkyl and R$_2$ is hydrogen or alkyl and the alkyl is optionally substituted.

"Amino" refers to the group —NH$_2$.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

A "halo" substituent is a monovalent halogen radical chosen from chloro, bromo, iodo, and fluoro. A "halogenated" compound is one substituted with one or more halo substituent.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. $C_x$ cycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

A "cyclic amino" is a monovalent radical of a saturated 5-, 6-, or 7-membered cyclic amine ring having no more than one additional hetero atom such as nitrogen, oxygen, or sulfur. Representative examples include, e.g., 1-pyrrolidino, 1-piperidino, morpholino, piperazino, 3-benzylpiperidino, and the like. These may be substituted or unsubstituted. If substituted, generally they will have no more than 2 substituents chosen from lower alkyl, lower cycloalkyl, hydroxy lower alkyl, phenyl (substituted or unsubstituted), benzyl (substituted or unsubstituted), aminocarbonylmethyl, lower alkylaminocarbonylmethyl, amino, mono- or di-lower alkylamino, cyclic amino, or a 5- or 6-membered heterocyclic ring.

Other chemical terms are given their standard meaning as understood by one of skill in the art with guidance from standard texts and dictionaries.

The term "MTD" is the abbreviation for maximum tolerated does.

The term "nM" is the abbreviation for nanomolar.

The term "ip" is the abbreviation for intraperitoneal.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease "Subject" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

The term "pharmaceutically acceptable" refers to safe and non-toxic for in vivo, preferably, for human administration.

"Pharmaceutically acceptable salt" refers to a salt that is pharmaceutically acceptable. Any compound described herein may be administered as a pharmaceutically acceptable salt.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Effective amount" or dose of a compound or a composition, refers to that amount of the compound or the composition that results in an intended result as desired based on the disclosure herein. Effective amounts can be determined by standard pharmaceutical procedures in cell cultures or experimental animals, e.g., and without limitation, by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$.

"Therapeutically effective amount" or dose of a compound or a composition refers to that amount of the compound or the composition that results in reduction or inhibition of symptoms or a prolongation of survival in a patient. The results may require multiple doses of the compound or the composition.

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The group may be substituted with one or more substituents, such as e.g., 1, 2, 3, 4 or 5 substituents. Preferably, the substituents are selected from the functional groups provided herein. In certain more preferred embodiments, the substituents are selected from oxo, halo, —CN, $NO_2$, —$CO_2R^{100}$, —$OR^{100}$, —$SR^{100}$, —$SOR^{100}$, —$SO_2R^{100}$, —$NR^{101}R^{102}$, —$CONR^{101}R^{102}$, —$SO_2NR^{101}R^{102}$, $C_1$-$C_6$ alkyl, $C_1$-$C_6$ alkoxy, —$CR^{100}$=C($R^{100})_2$, —$CCR^{100}$, $C_3$-$C_{10}$ cycloalkyl, $C_3$-$C_{10}$ heterocyclyl, $C_6$-$C_{12}$ aryl and $C_5$-$C_{12}$ heteroaryl, wherein each $R^{100}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. More preferably, the substituents are selected from the group consisting of chloro, fluoro, —$OCH_3$, methyl, ethyl, isopropyl, cyclopropyl, —$OCF_3$, —$CF_3$ and —$OCHF_2$.

$R^{101}$ and $R^{102}$ independently are hydrogen; $C_1$-$C_8$ alkyl, optionally substituted with —$CO_2H$ or an ester thereof, $C_1$-$C_6$ alkoxy, oxo, —$CR^{103}$=C($R^{103})_2$, —CCR, $C_3$-$C_{10}$ cycloalkyl, $C_3$-$C_{10}$ heterocyclyl, $C_6$-$C_{12}$ aryl, or $C_2$-$C_{12}$ heteroaryl, wherein each $R^{103}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; wherein each cycloalkyl, heterocyclyl, aryl, or heteroaryl is optionally substituted with 1-3 alkyl groups or 1-3 halo groups, or $R^{101}$ and $R^{102}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment.

For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds

In one aspect, provided herein is a compound of formula (I):

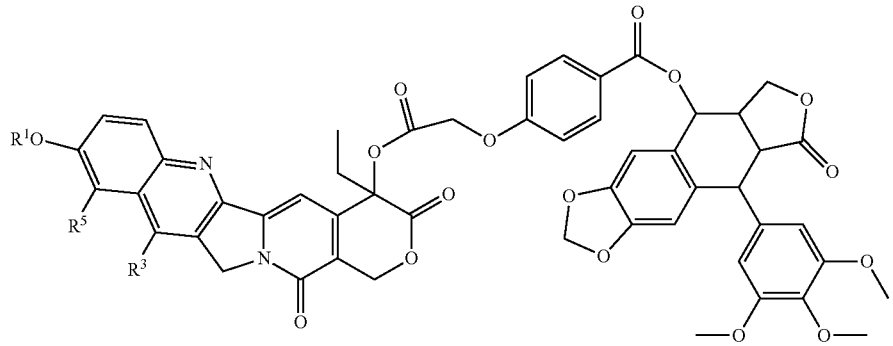

or an N-oxide thereof, or a pharmaceutically acceptable salt of each thereof, or a pharmaceutically acceptable solvate of each of the foregoing, wherein $R^1$ is H or has a structure of:

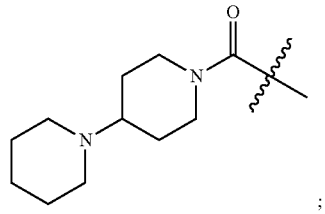 [SMILES: *C(=O)N1CCC(N2CCCCC2)CC1]

$R^3$ is H, an optionally substituted $C_1$-$C_8$ alkyl, an optionally substituted 3-10 membered cycloalkyl, an optionally substituted 3-10 membered heterocyclyl, an optionally substituted 6-10 membered aryl, or an optionally substituted 5-10 membered heteroaryl;

$R^5$ is H or has a structure of:

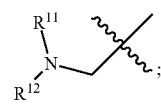

and $R^{11}$ and $R^{12}$ independently is an optionally substituted $C_1$-$C_8$ alkyl.

In one embodiment, $R^1$ is H. In another embodiment, $R^1$ has a structure of:

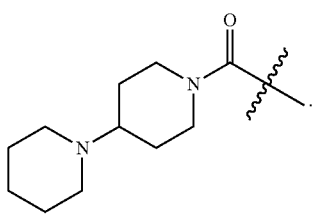 [SMILES: *C(=O)N1CCC(N2CCCCC2)CC1]

In one embodiment, $R^5$ is H. In another embodiment, $R^5$ is:

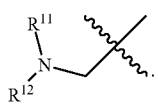

In one embodiment, $R^{11}$ is an optionally substituted $C_1$-$C_8$ alkyl. In another embodiment, $R^{11}$ is $C_1$-$C_8$ alkyl. In another embodiment, $R^{11}$ is methyl.

In one embodiment, $R^{12}$ is an optionally substituted $C_1$-$C_8$ alkyl. In another embodiment, $R^{12}$ is $C_1$-$C_8$ alkyl. In another embodiment, $R^{12}$ is methyl.

In one embodiment, $R^3$ is H. In one embodiment, $R^3$ is an optionally substituted $C_1$-$C_8$ alkyl. In another embodiment, $R^3$ is $C_1$-$C_8$ alkyl. In another embodiment, $R^3$ is an optionally substituted 3-10 membered cycloalkyl. In another embodiment, $R^3$ is an optionally substituted 3-10 membered heterocyclyl. In another embodiment, $R^3$ is an optionally substituted 6-10 membered aryl. In another embodiment, $R^3$ is an optionally substituted 5-10 membered heteroaryl. In another embodiment, $R^3$ is ethyl.

In one embodiment, the compound of formula (I) has the structure of:

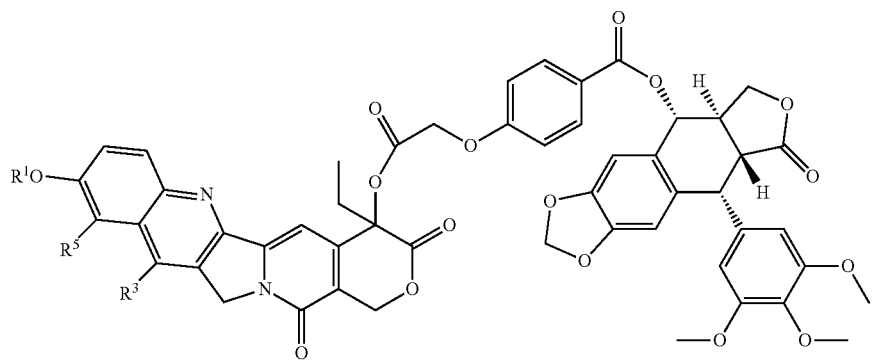

wherein the variables are defined as above.

In one embodiment, the compound of formula (I) is:

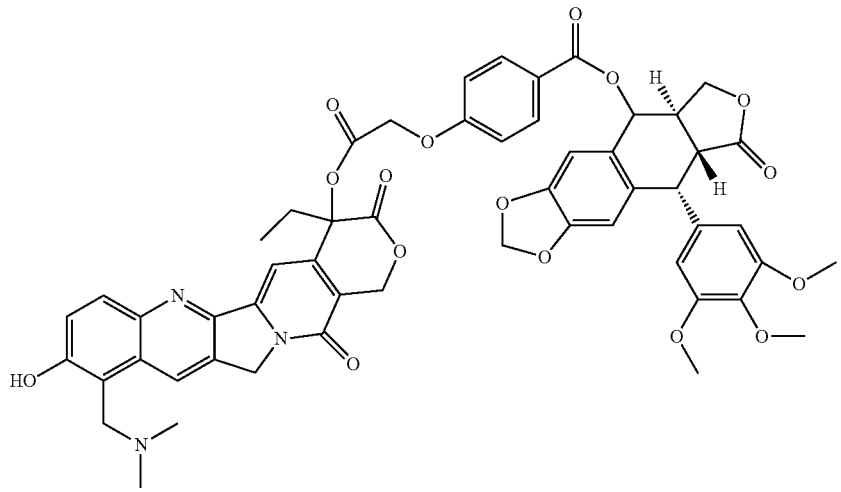 [SMILES: CCC1(OC(=O)COc2ccc(C(=O)OC3c4cc5c(cc4[C@@H](c4cc(OC)c(OC)c(OC)c4)[C@H]4C(=O)OC[C@H]34)OCO5)cc2)C(=O)OCc2c1cc1n(c2=O)Cc2cc3c(CN(C)C)c(O)ccc3nc2-1]

or an N-oxide thereof, or a pharmaceutically acceptable salt of each thereof, or a pharmaceutically acceptable solvate of each of the foregoing.

In one embodiment, the compound of formula (I) is:

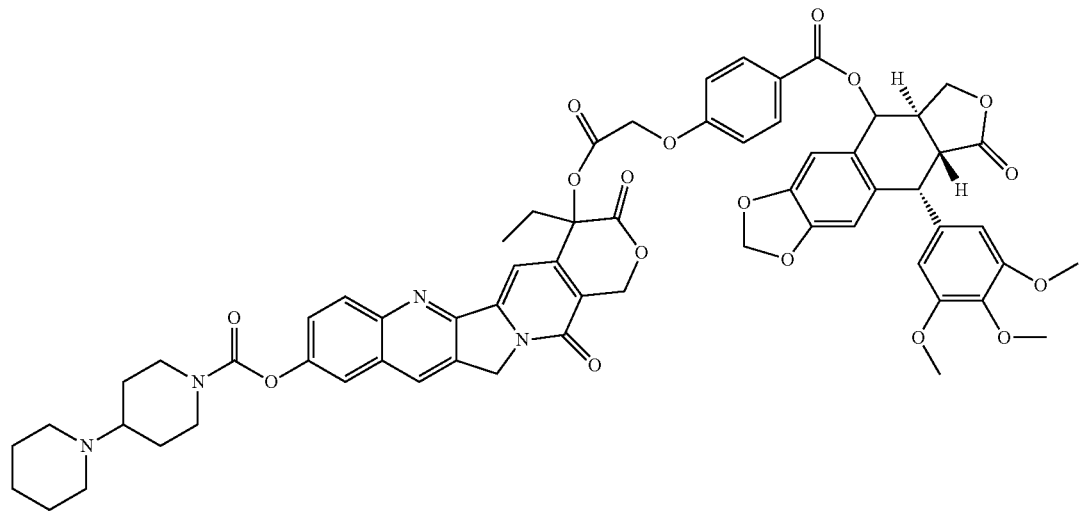 [SMILES: CCC1(OC(=O)COc2ccc(C(=O)OC3c4cc5c(cc4[C@@H](c4cc(OC)c(OC)c(OC)c4)[C@H]4C(=O)OC[C@H]34)OCO5)cc2)C(=O)OCc2c1cc1n(c2=O)Cc2cc3cc(OC(=O)N4CCC(N5CCCCC5)CC4)ccc3nc2-1]

or an N-oxide thereof, or a pharmaceutically acceptable salt of each thereof, or a pharmaceutically acceptable solvate of each of the foregoing.

In one embodiment, the compound of formula (I) is:

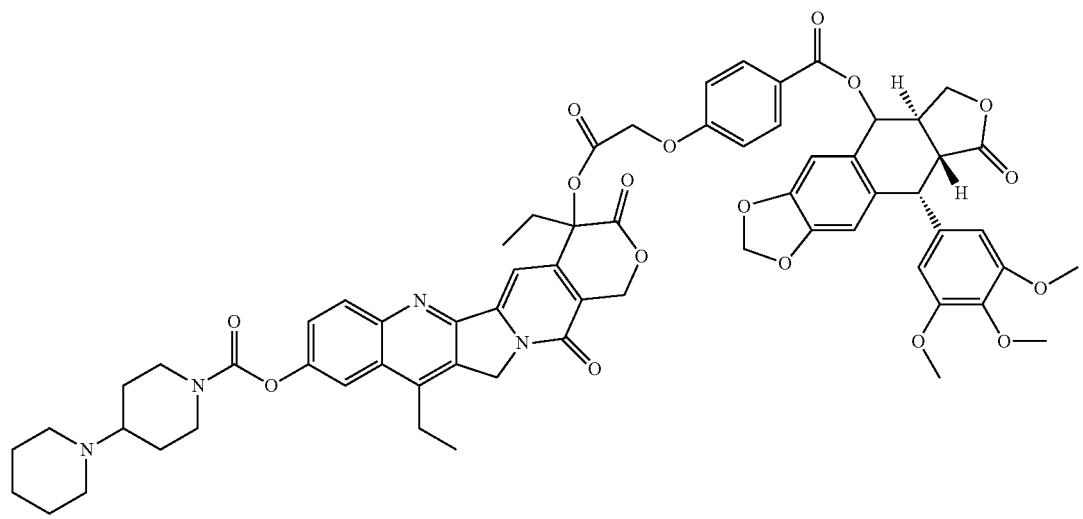 [SMILES: CCc1c2c(nc3ccc(OC(=O)N4CCC(N5CCCCC5)CC4)cc13)-c1cc3c(c(=O)n1C2)COC(=O)C3(CC)OC(=O)COc1ccc(C(=O)OC2c3cc4c(cc3[C@@H](c3cc(OC)c(OC)c(OC)c3)[C@H]3C(=O)OC[C@H]23)OCO4)cc1]

or an N-oxide thereof, or a pharmaceutically acceptable salt of each thereof, or a pharmaceutically acceptable solvate of each of the foregoing.

In one embodiment, the compound of formula (I) is:

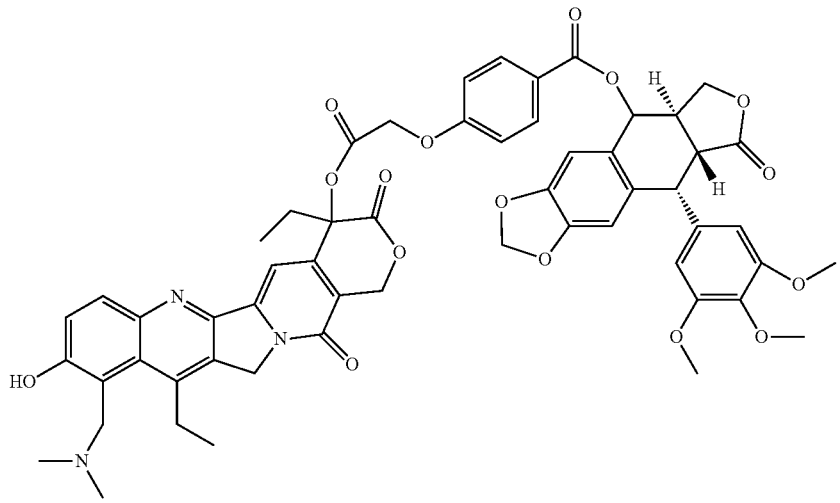 [SMILES: CCc1c2c(nc3ccc(O)c(CN(C)C)c13)-c1cc3c(c(=O)n1C2)COC(=O)C3(CC)OC(=O)COc1ccc(C(=O)OC2c3cc4c(cc3[C@@H](c3cc(OC)c(OC)c(OC)c3)[C@H]3C(=O)OC[C@H]23)OCO4)cc1]

or or an N-oxide thereof, or a pharmaceutically acceptable salt of each thereof, or a pharmaceutically acceptable solvate of each of the foregoing.

In one embodiment, provided herein are individual stereoisomers, such as enantiomers, of the compounds provided herein. In one embodiment, the compounds provided herein have a stereochemical configuration as shown below:
or

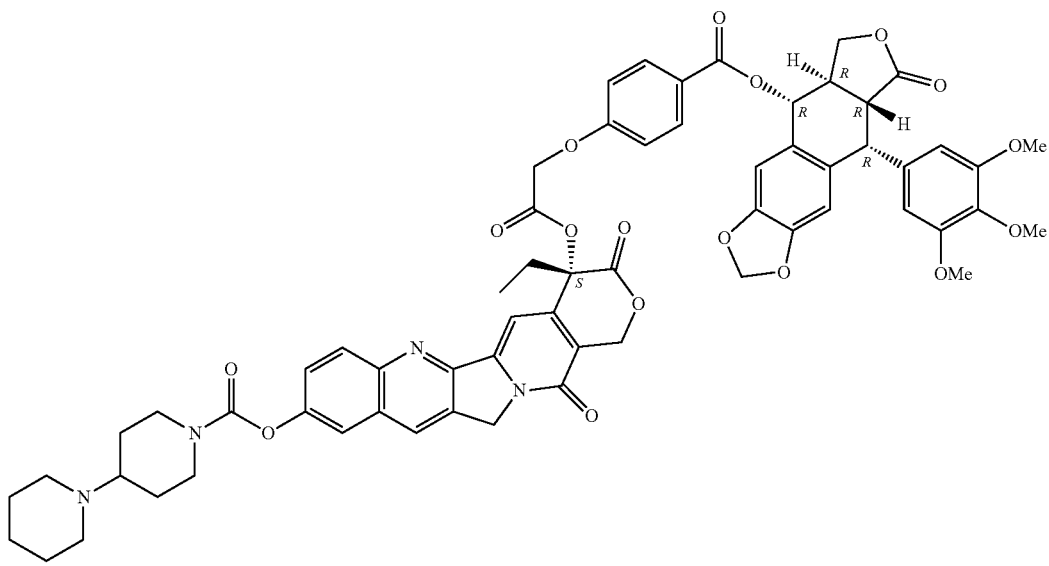

Podophyllotoxin derivatives can be prepared by the skilled artisan based on methods described herein and/or in U.S. Pat. No. 8,158,809, or adapting those methods.

Pharmaceutical Composition

In another aspect, provided herein is a pharmaceutical composition comprising a compound provided herein, and at least one pharmaceutically acceptable excipient.

In one embodiment, the pharmaceutical composition is a solid form, liquid form, injectable form, or a liposomal formulation. In another embodiment, the pharmaceutical composition is a solid form. In another embodiment, the pharmaceutical composition is a liquid form. In another embodiment, the pharmaceutical composition is an injectable form. In another embodiment, the pharmaceutical composition is a liposomal formulation. In another embodiment, the pharmaceutical composition is a micelle formulation.

This aspect of the disclosure is a pharmaceutical composition useful for treating cancer in a warm-blooded animal, which composition comprises compound of the disclosure as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the 18$^{th}$ or 19$^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will preferably contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5.0 to about 50% by weight (% w) in dosage units weighing between 5 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

A compound may be administered parenterally, e.g., intravenously, intramuscularly, intravenously, subcutaneously, or intraperitoneally. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In one embodiment, the compositions provided here are for injection, such as solutions for injection. In one embodiment, the compounds provided herein can be administered as an injectable solution. In one embodiment, the injectable solution comprises at least one pharmaceutically acceptable excipient. In one embodiment, the pharmaceutically acceptable excipient is one or more of D-mannitol, L-lactic acid, a pH adjusting agent, and sterile water. A non-limiting example of a pH adjusting agent is sodium hydroxide. In one embodiment, Compound 801.HCl is administered as an injectable solution (see Table A below).

TABLE A

Formulated Bulk Solution: (20 L/20.00 kg)
Final Product Fill: 5.00 ± 0.10 g

| Component | Reference to Quality | Amount per batch | Amount per vial | Concentration |
|---|---|---|---|---|
| 801•HCl Formulate$^a$ | Meets specification | 697.7 g (formulate) | 30.0 mg (free base) 174.4 mg (formulate) | 6 mg/mL (free base) 34.9 mg (formulate) |

TABLE A-continued

Formulated Bulk Solution: (20 L/20.00 kg)
Final Product Fill: 5.00 ± 0.10 g

| Component | Reference to Quality | Amount per batch | Amount per vial | Concentration |
|---|---|---|---|---|
| d-Mannitol | USP | 168.0 g | 42.0 mg | 8.4 mg/mL |
| L-Lactic acid | USP | 18.02 g | 4.50 mg | 0.901 mg/mL |
| Sodium hydroxide | NF | As needed to adjust pH to 3.5 | As needed | As needed |
| Sterile water for injection | USP | QS to 20.00 kg | QS to 5.00 mL | QS to 1 mL |

$^a$801•HCl Formulate = 801 free base•HCl•2 MPEG-2000-DSPE
QS = quantity sufficient In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Although the compounds of this disclosure tend to be water soluble, in some cases, e.g., where a compound of the invention is less water soluble, it may be useful to provide liposomal delivery. The system restrains the compound of the invention by incorporating, encapsulating, surrounding, or entrapping the compound of the invention in, on, or by lipid vesicles or liposomes, or by micelles.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255-3261; Perex-Soler, et al., *Cancer Res.* 1990, 50: 4260-4266; and, Khokhar, et al., *J. Med. Chem.* 1991, 34: 325-329, all of which are incorporated herein in their entireties by reference.

Similarly, micelles have also been used to deliver medications to patients, (Broden et al., *Acta Pharm Suec.* 19: 267-284 (1982)) and micelles have been used as drug carriers and for targeted drug delivery, (D. D. Lasic, *Nature* 335: 279-280 (1992); and, Supersaxo et al., *Pharm Res.* 8: 1280-1291 (1991)), including cancer medications, (Fung et al., *Biomater. Artif Cells. Artif Organs* 16: 439 et seq. (1988); and Yokoyama et al., *Cancer Res.* 51: 3229-3236 (1991)), all of which are incorporated herein in their entireties by reference.

The liposomes and/or micelles containing the compound of the invention can be administered to a cancer patient, typically intravenously. Further guidance for preparing liposomal compositions useful in this invention may be found in U.S. Pat. No. 6,096,336, which is incorporated herein by reference.

Methods of Treatment

In another aspect, provided herein is a method of treating cancer in a subject in need thereof comprising administering to the subject a therapeutically effective amount of a compound provided herein.

In one embodiment, the therapeutically effective amount of the compound administered is about 15 mg/m$^2$ to about 1500 mg/m$^2$. In another embodiment, the therapeutically effective amount of a compound the compound administered is about 50 mg/m$^2$ to about 1000 mg/m$^2$. In another embodiment, the therapeutically effective amount of the compound administered is about 100 mg/m$^2$ to about 750 mg/m$^2$. In another embodiment, the therapeutically effective amount of the compound administered is about 250 mg/m$^2$ to about 500 mg/m$^2$.

In one embodiment, the cancer is colon cancer, non-small lung cancer, chronic myeloid leukemia, acute myeloid leukemia, small cell lung cancer, cervical cancer, stomach cancer, breast cancer, prostate cancer, skin cancer, melanoma, lymphoma, brain tumor, sarcoma, testicle cancer, ovarian cancer, renal cancer, head and neck cancer, liver cancer, leukemia, acute lymphoblastic leukemia, chronic lymphoblastic leukemia, hairy cell leukemia, T-cell prolymphocytic leukemia, large granular lymphocytic leukemia, adult T-cell leukemia, and a blood cancer.

In one embodiment, the cancer comprises a solid tumor.

In another aspect, provided herein is a method of delaying or regressing tumor growth in a subject in need thereof comprising administering to the subject a therapeutically effective amount of a compound provided herein.

In one embodiment, the tumor growth is a solid tumor.

In one embodiment, the cancer is colon cancer, non-small lung cancer, chronic myeloid leukemia, acute myeloid leukemia, small cell lung cancer, cervical cancer, stomach cancer, breast cancer, prostate cancer, skin cancer, melanoma, lymphoma, brain tumor, sarcoma, testicle cancer, ovarian cancer, renal cancer, head and neck cancer, liver cancer, leukemia, acute lymphoblastic leukemia, chronic lymphoblastic leukemia, hairy cell leukemia, T-cell prolymphocytic leukemia, large granular lymphocytic leukemia, adult T-cell leukemia, and a blood cancer.

In another aspect, provided herein is a method of treating cancer in a subject in need thereof comprising administering to the subject a therapeutically effective amount of a pharmaceutical composition provided herein.

In one embodiment, the cancer is colon cancer, non-small lung cancer, chronic myeloid leukemia, acute myeloid leukemia, small cell lung cancer, cervical cancer, stomach cancer, breast cancer, prostate cancer, skin cancer, melanoma, lymphoma, brain tumor, sarcoma, testicle cancer, ovarian cancer, renal cancer, head and neck cancer, liver cancer, leukemia, acute lymphoblastic leukemia, chronic lymphoblastic leukemia, hairy cell leukemia, T-cell prolymphocytic leukemia, large granular lymphocytic leukemia, adult T-cell leukemia, and a blood cancer.

In one embodiment, the cancer comprises a solid tumor.

A compound useful in this disclosure is administered to an appropriate subject in need of these compounds in a therapeutically effective dose by a medically acceptable route of administration such as orally, parentally (e.g., intramuscularly, intravenously, subcutaneously, interperitoneally), transdermally, rectally, by inhalation and the like.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W.B. Saunders Company). This information from Chapter 8 is incorporated herein by reference. The following Table B provides examples of the types of cancers, i.e., malignant tumors or neoplasia that may be treated by administering a compound of this disclosure.

TABLE B

| Tissue of Origin | Malignant |
| --- | --- |
| Composed of One Parenchymal Cell Type Mesenchymal tumors | |
| Connective tissue and derivatives | Fibrosarcoma |
| | Liposarcoma |
| | Chondrosarcome |
| | Osteogenic sarcoma |
| Endothelial and related tissues | |
| Blood vessels | Angiosarcoma |
| Lymph vessels | Lymphangiosarcoma |
| Synovium | Synovial sarcoma |
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Striated | Rhabdomyosarcoma |
| Epthelial tumors | |
| Stratified squamous | Squamous cell or epidermoid carcinoma |
| Basal cells of skin or adnexa | Basal cell carcinoma |
| Epithelial lining | |
| Glands or ducts | Adenocarcinoma |
| | Papillary carcinoma |
| | Cystadenocarcinoma |
| Respiratory passages | Bronchogenic carcinoma |
| | Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma |
| | Embryonal carcinoma |
| More Than One Neoplastic Cell - Mixed Tumors, Usually Derived From One Germ Layer | |
| Salivary glands | Malignant mixed tumor of salivary gland origin |
| Breast | Malignant cystosarcoma phyllodes |

TABLE B-continued

| Tissue of Origin | Malignant |
| --- | --- |
| Renal anlage | Wilms tumor |
| More Than One Neoplastic Cell Type Derived From More Than One Germ Layer - Teratogenous | |
| Totipotential cells in gonads or in embryonic rests | Immature teratoma, teratocarcinoma |

The compounds of the disclosure are thus useful in the treatment of leukemia and solid tumors, such as colon, colo-rectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a "therapeutically effective amount" of podophyllotoxin derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on mg/m$^2$ of body surface) is described by E. J. Freireich et al., Cancer Chemother. Rep., 50(4):219 (1966). Body surface area may be approximately determined from the height and weight of an individual (see, e.g., Scientific Tables, Geigy Pharmaceuticals, Ardsley, N.Y. pp. 537-538 (1970)). A suitable dose range is from 1 to 1000 mg of equivalent per m$^2$ body surface area of a compound of the invention, for instance from 50 to 500 mg/m$^2$.

For all of the administering routes, the exact timing of administration of the dosages can be varied to achieve optimal results. Generally, if using Intralipid 20 as the carrier for the derivative, the actual dosage of derivative reaching the patient will be less. This is due to some loss of the derivative on the walls of the syringes, needles and preparation vessels, which is prevalent with the Intralipid 20 suspension. When a carrier, such as cottonseed oil is used, this above described loss is not so prevalent because the derivative does not adhere as much to the surface of syringes, etc.

Another important feature of the method provided by the present disclosure relates to the relatively low apparent overall toxicity of the derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

EXAMPLES

Example 1: Synthesis of N2

Scheme 1.

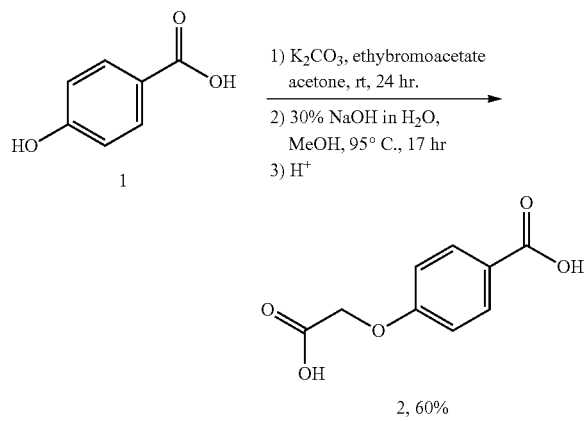

4-carboxyphenoxy acetic acid (2). To a suspension of 4-hydroxybenzoic acid (50 g, 361.4 mmol) and $K_2CO_3$ (200 g, 1.45 mol) in acetone (720 mL) was added ethyl bromoacetate (140 mL, 1.27 mol). After stirring at room temperature for 24 hr, the mixture was filtered and concentrated (60 torr, 40° C. bath temperature). The remaining thick oil was dissolved in MeOH (720 mL) and added a solution of 30% wt/v NaOH in Water (108 g NaOH in 360 mL $H_2O$). The mixture was refluxed at 95° C. for 17 hr. The mixture was cooled to 0° C. and concentrated HCl (350 mL) was added slowly while stirring. Once the addition was completed, the mixture was filtered and the precipitate was washed with water (1×100 mL) and acetone (2×100 mL), followed by drying under high vacuum at 40° C. for 4 days to afford 42.5 g of product as white solid (60%). ESIMS: calcd for $C_9H_8O_5$ [M+H]$^+$ 197.04, found 197.1.

Camptothecin-10-O-[4-piperidinopiperidine]carbamate (4)

The 4-piperidinopiperidinecarbamyl chloride reagent was prepared according to the literature condition (U.S. Pat. No. 6,121,451. Briefly, To a solution of 4-piperidinopiperidine (35 g, 208 mmol) in DCM (2.6 L) at 0° C. was added a solution of triphosgene (22.1 g, 83.2 mmol) in DCM (300 mL) slowly. The mixture was stirred from 0° C. to rt for 17 hr. Celite was added and the solution was filtered. The filtrate was washed with 7% wt/v $NaHCO_3$ solution and dried over $MgSO_4$ (100 g). The mixture was filtered and the solvent evaporated. The remaining residue was dissolved in anhydrous DCM (208 mL) to make 1M solution. The solution was used as is without further purification.

The 10-hydroxycamptothecin (25 g, 68.5 mmol) was dissolved in 1:1 DCM/pyridine (1.37 L) and added the freshly prepared 4-piperidinopiperidinecarbamyl chloride solution (208 mL). After stirring at rt for 4 hr, the reaction mixture was concentrated and purified by silica gel chromatography (600 g) with 10% MeOH/DCM (7 L) to give 38 g of product as light yellow solid (100%). ESIMS: calcd for $C_{31}H_{34}N_4O_6$ [M+H]$^+$ 559.25, found 559.0.

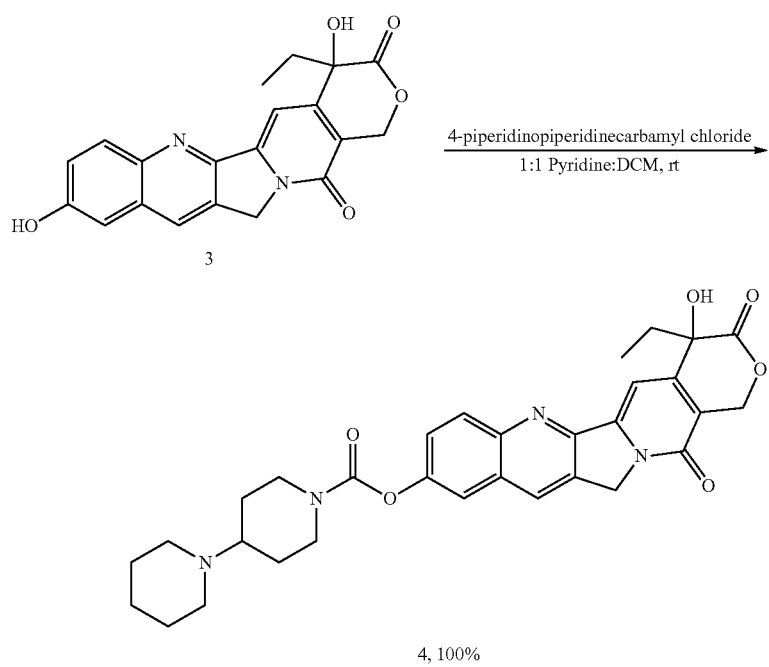

Scheme 3.

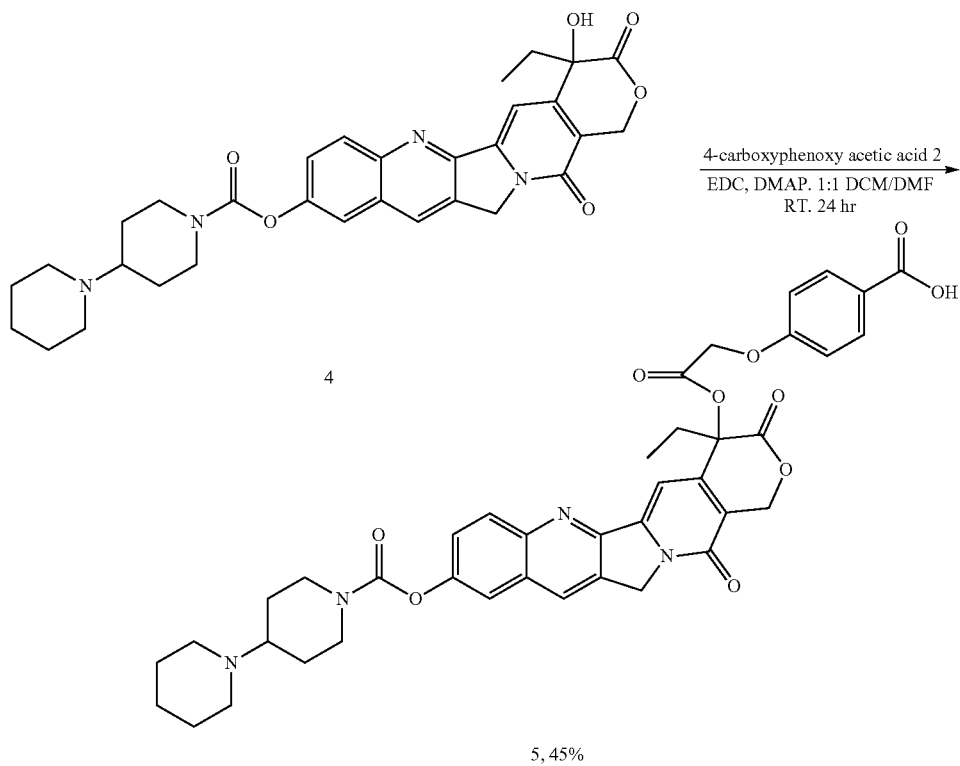

Camptothecin-10-O-[4-piperidinopiperidine]car-bamyl]-20-O-[4-carboxyphenoxy]acetic acid. (5)

Camptothecin-10-O-[4-piperidinopiperidine]carbamate (4, 38 g, 68.5 mmol), EDC (61.4 g, 319.6 mmol), DMAP (4.85 g, 79.9 mmol) and 4-carboxyphenoxy acetic acid (2, 39.2 g, 199.7 mmol) were dissolved in 1:1 DCM/DMF (2.66 L). After stirring at rt for 22 hr, the mixture was concentrated and the remaining residue was dissolved in DCM (3 L) and washed with saturated NaHCO$_3$ solution (2×200 mL) followed by water (2×200 mL). The aqueous phase was combined and extracted with DCM (2×200 mL). The organic layer and the organic extracts were combined, dried over MgSO$_4$ (100 g), filtered and the solvent evaporated. The remaining residue was purified by silica gel chromatography (1 kg) with 10% MeOH/DCM+1% AcOH (2 L), 20% MeOH/DCM+2% AcOH (5 L), and 30% MeOH/DCM+3% AcOH (4 L). The product containing fractions were combined and the solvent evaporated. The crude product was dissolved in 10% MeOH/DCM (100 mL) and the solution was added to MeOH (500 mL). The mixture was stirred at rt for 30 min and the resulting precipitate was collected by filtration to give 22.4 g of product as light yellow solid (45%). ESIMS: calcd for $C_{40}H_{40}N_4O_{10}$ [M+H]$^+$ 737.27, found 737.0. Note: this step can be improved further and we should be able to get ~70% yield.

Scheme 4.

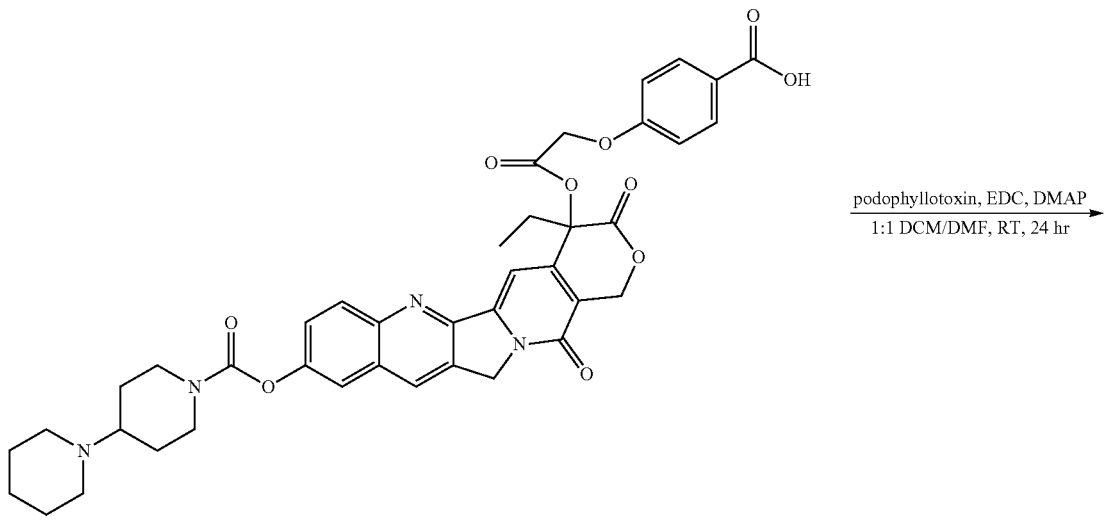

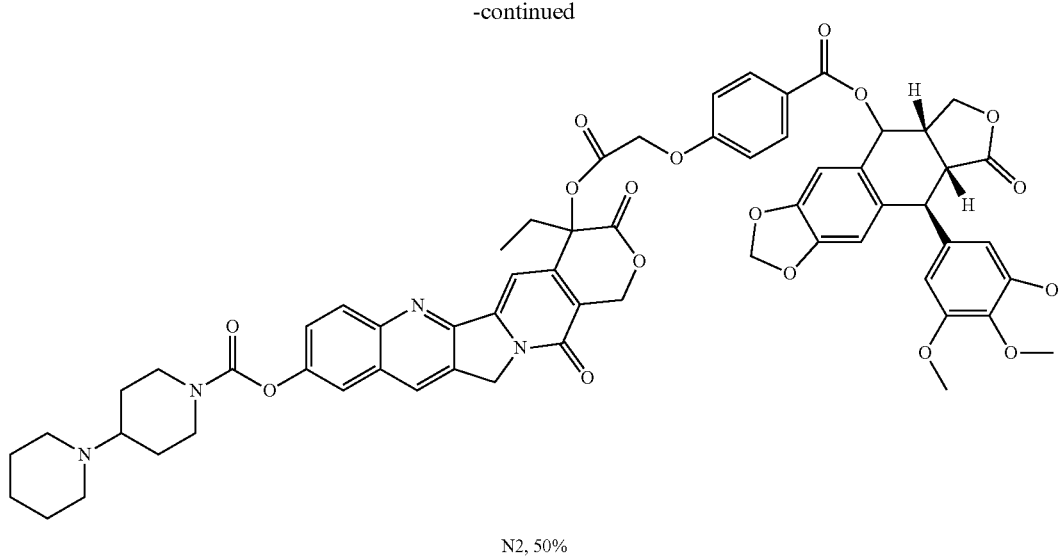

N2, 50%

N2

EDC (17.53 g, 91.3 mmol), DMAP (3.71 g, 30.4 mmol), 5 (22.4 g, 30.4 mmol) and podophyllotoxin (25.2 g, 60.9 mmol) were dissolved in 1:1 DCM/DMF (1.52 L) and the mixture was stirred at rt for 24 hr. The reaction mixture was diluted with DCM (2 L), washed with saturated NaHCO$_3$ solution (2×500 mL), water (1x 500 mL), dried over MgSO$_4$ (100 g), filtered and the solvent evaporated. The remaining residue was purified by Silica gel column chromatography (900 g) with 5% MeOH/DCM (2 L) and 7.5% MeOH/DCM (6 L). The product containing fractions were collected and the solvent was evaporated. The pure product was acidified by dissolving in 10% MeOH/DCM (50 mL) followed by addition of 4M HCl in dioxane (25 mL). The mixture was added slowly to stirred Et$_2$O (750 mL). The precipitate was filtered and dried under high vacuum overnight. Recovered 17.5 g of N2 hydrochloride salt as yellow solid (50%). ESIMS: calcd for C$_{62}$H$_{60}$N$_4$O$_{17}$ [M+H]$^+$ 1133.40, found 1133.0.

Figure 2:
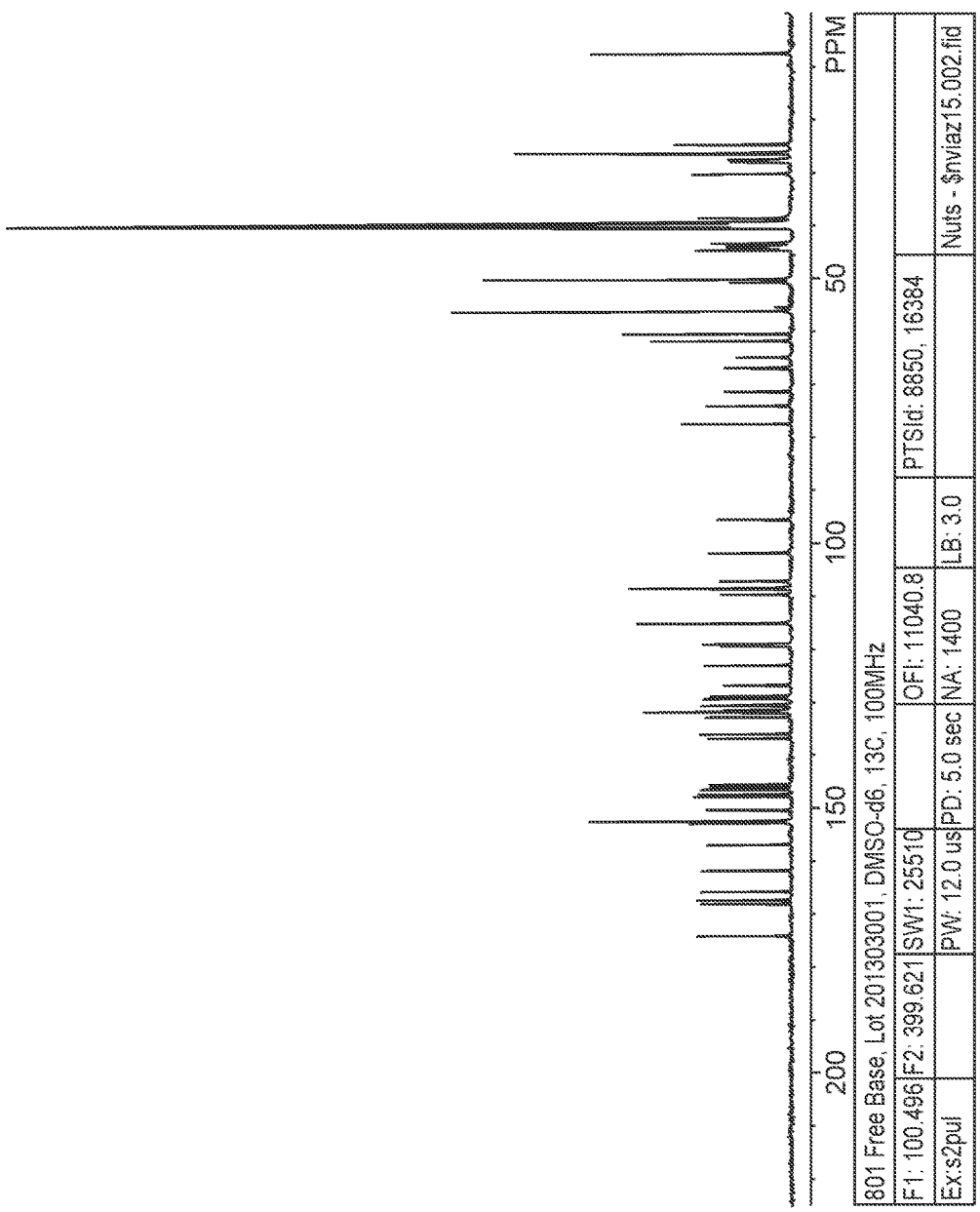
FIG. 2 shows the $^{13}$C Nuclear Magnetic Resonance spectrum of N2.
Figure 3A:
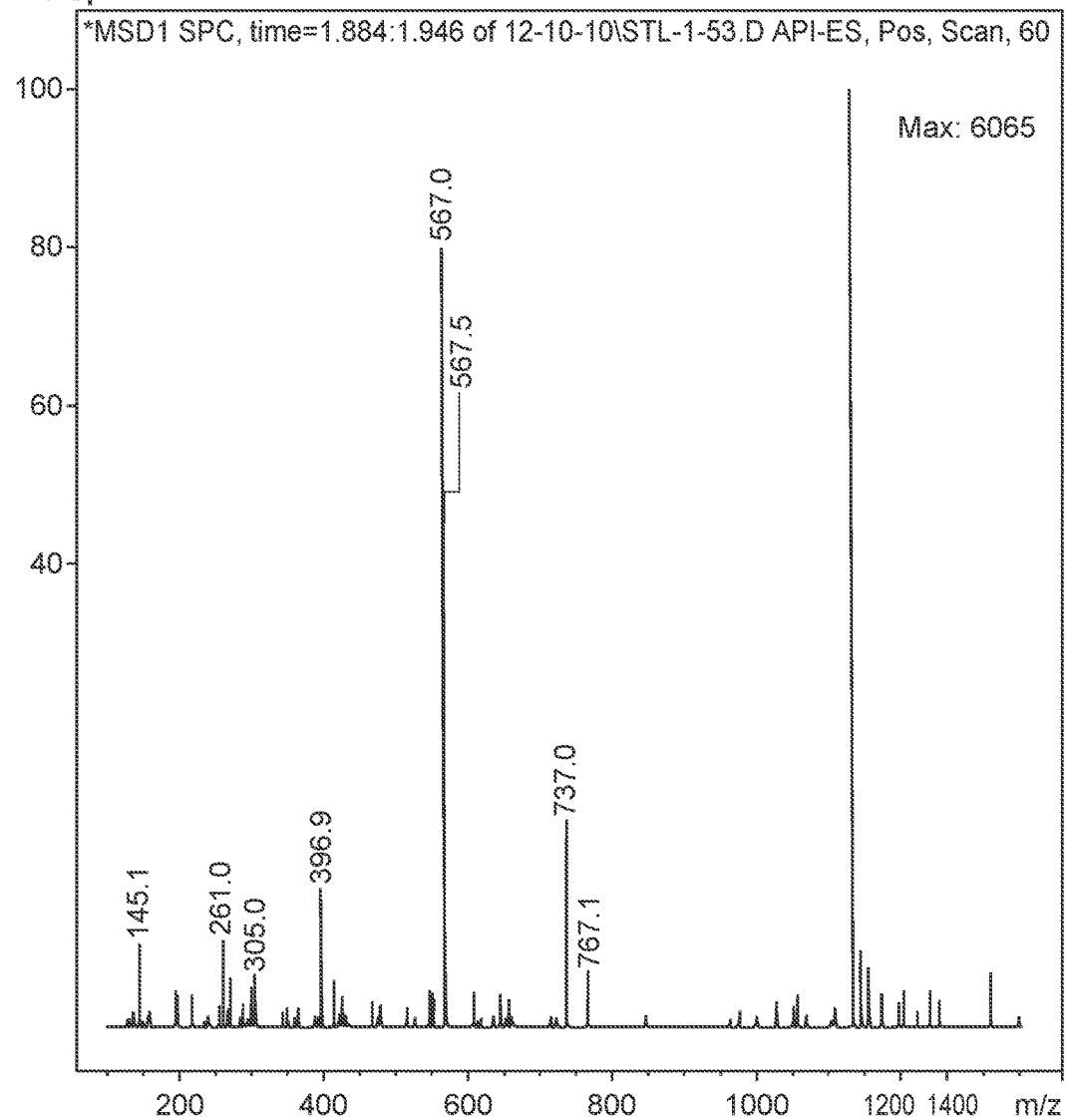
FIGS. 3A-3D show the Liquid Chromatography-Mass Spectra of N2 and Target Compounds 1, 3, and 4 respectively.

The $^1$H NMR and $^{13}$C NMR spectra of N2 are shown in FIGS. 1A and 2 respectively. The LC-MS spectrum of N2 is shown in FIG. 3A.

Example 2: Synthesis of N2.HCl Formulate

Scheme 5.

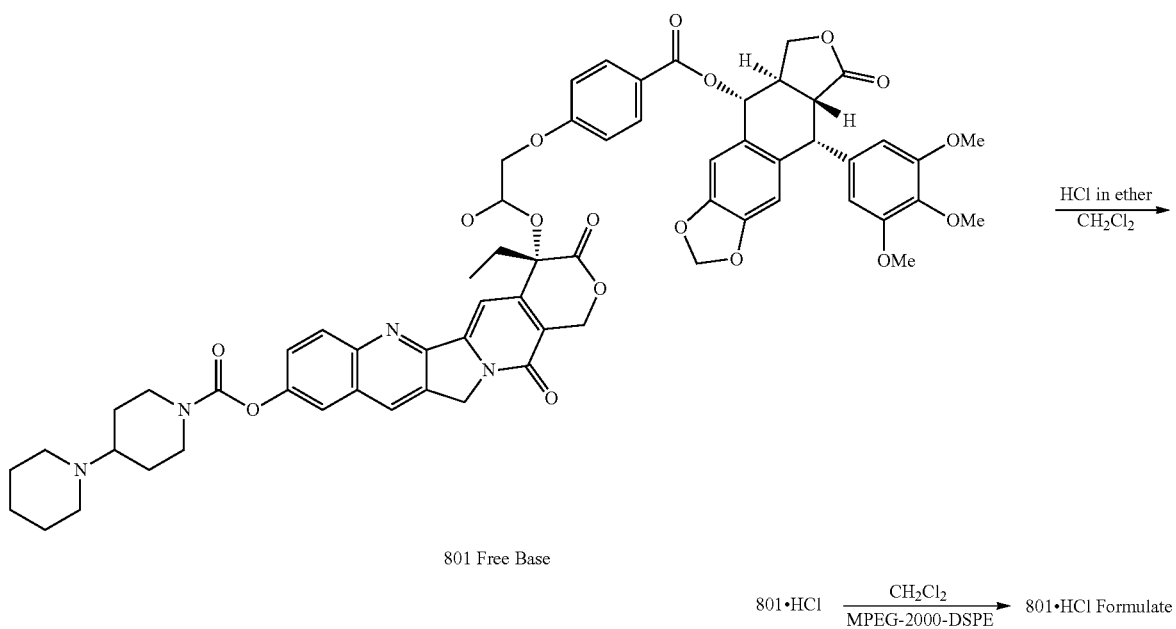

-continued

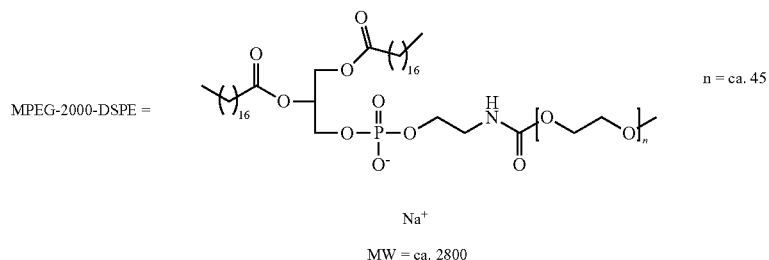

The N2.HCl formulate was prepared by the process shown in Scheme 5. To a filtered solution of N2 free base (1 equiv) in dichloromethane (ACS) at 10±5° C. was added HCl in ether (ACS, 1 M, 1.3 equiv). The solvent was removed in vacuo. To the residue was added a solution of MPEG-2000-DSPE (cGMP, 2 equiv) in dichloromethane. The mixture was agitated to obtain a clear solution and then the solvent was removed in vacuo. The residue was dissolved in dichloromethane, concentrated to dryness, dried under vacuum at room temperature until dichlormethane NMT 600 ppm by GC, micronized with a blender and screened with a 0.35 mm sieve to afford N2.HCl Formulate, lot #011000, 2.45 kg.

Example 3: Preparation of N2-HCl for Injection

L-Lactic acid solution (0.01 M, pH 3.5) was prepared by combining sterile water for injection (SWI, 18±0.5 kg) and L-lactic acid (18.02 g), adding 0.5 N sodium hydroxide until the pH of the solution is 3.5±0.1 and adding sufficient SWI to bring the total quantity of solution to 20.00 kg. The pH was adjusted to 3.5±0.1 by addition of 0.5 N sodium hydroxide.

A mixture of N2.HCl Formulate (697.7 g) and 0.01 M L-lactic acid solution, pH 3.5 (17±0.2 kg) was stirred until a solution was obtained. d-Mannitol (168.0 g) was added with mixing. The pH of the resulting solution was adjusted to 3.5±0.1 by addition of 0.5 N sodium hydroxide. Sufficient 0.01 M L-lactic acid solution, pH 3.5 was added to bring the total quantity of solution to 20.00 kg. The pH was adjusted to 3.5±0.1 by addition of 0.5 N sodium hydroxide. The solution was filtered through a 0.22 micron sterile filter into a sterile carboy and then filled into sterile 10 mL vials with 5.00±0.10 g per vial. Lyophilization was performed under sterile conditions ending at +25° C. and 100 mTorr. The vacuum was broken with nitrogen NF and sterile seals applied to the vials, which were stored at 2-8° C.

Example 4: Synthesis of Target Compound 1

Scheme 6.

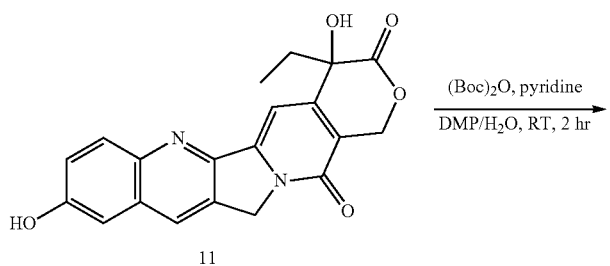

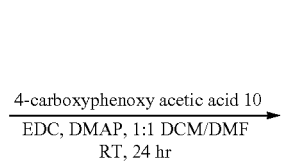

Figure 1B:
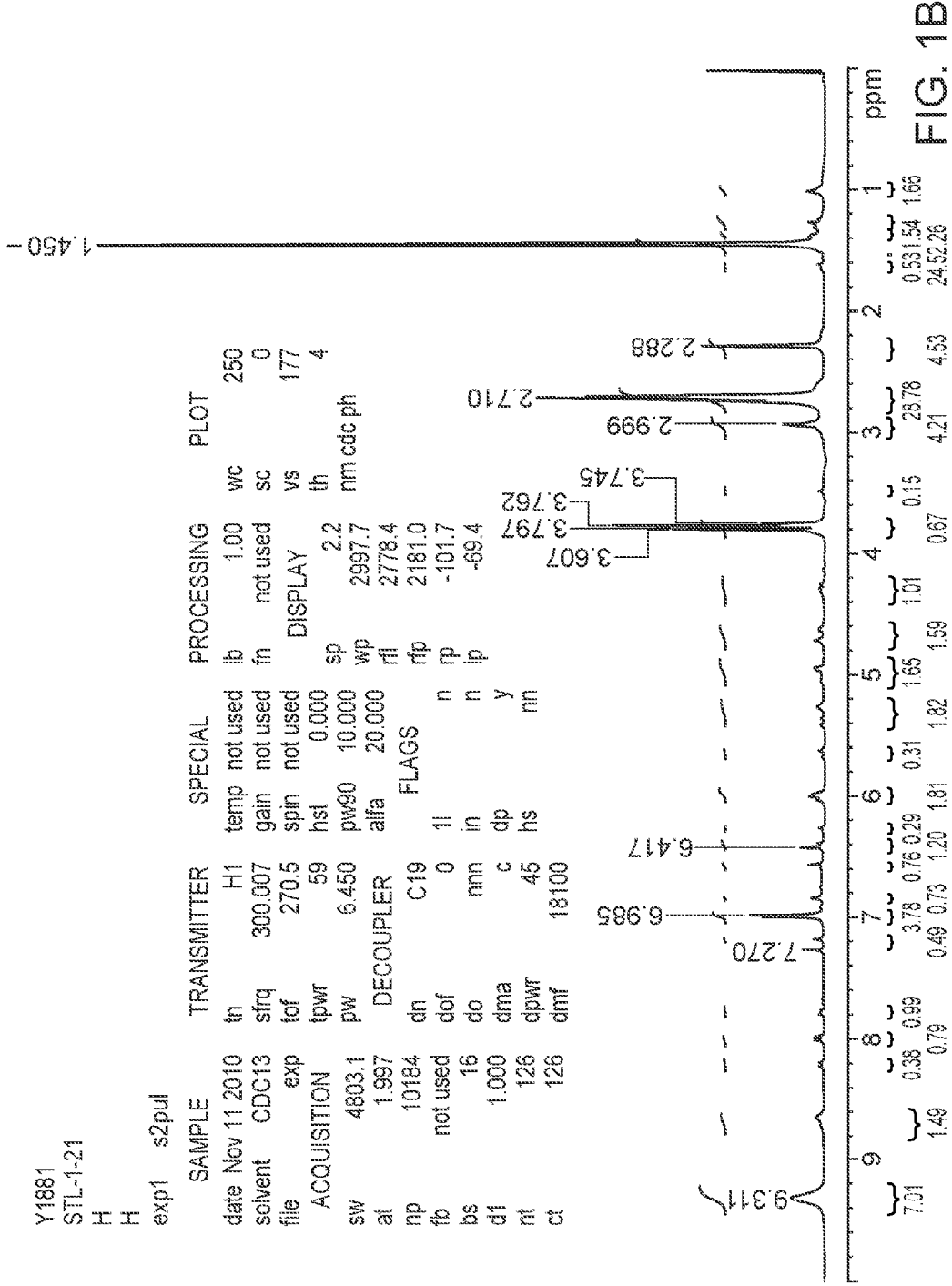
FIGS. 1B and 1F show the $^1$H Nuclear Magnetic Resonance spectra of Target Compounds 1 and 4 respectively.
Figure 1C:
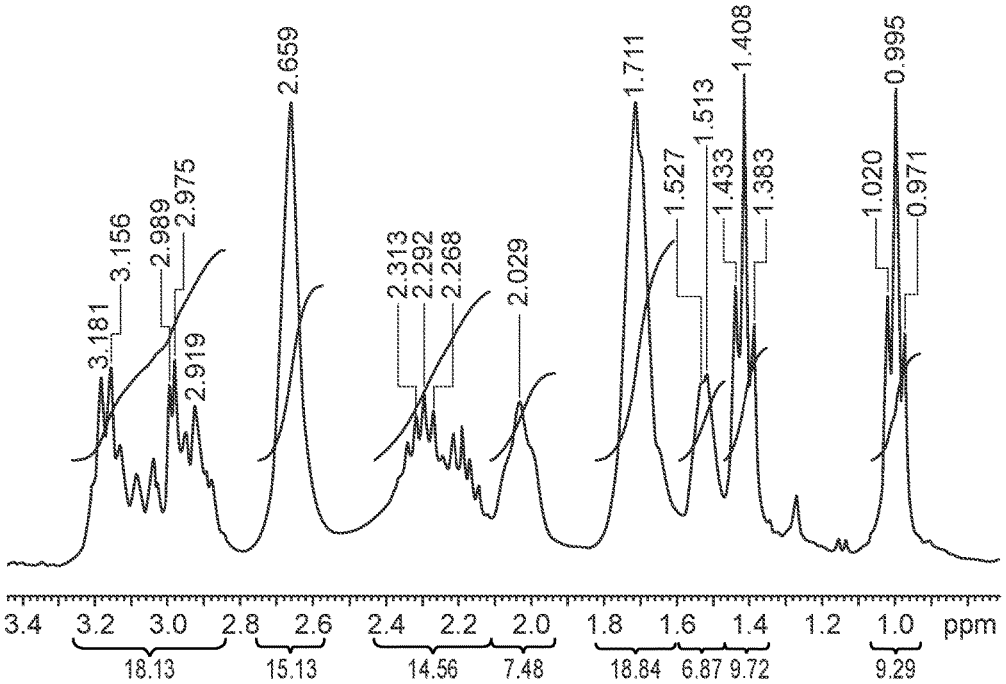
FIGS. 1C-1E show the $^1$H Nuclear Magnetic Resonance spectra of Target Compound 3.
Figure 1D:
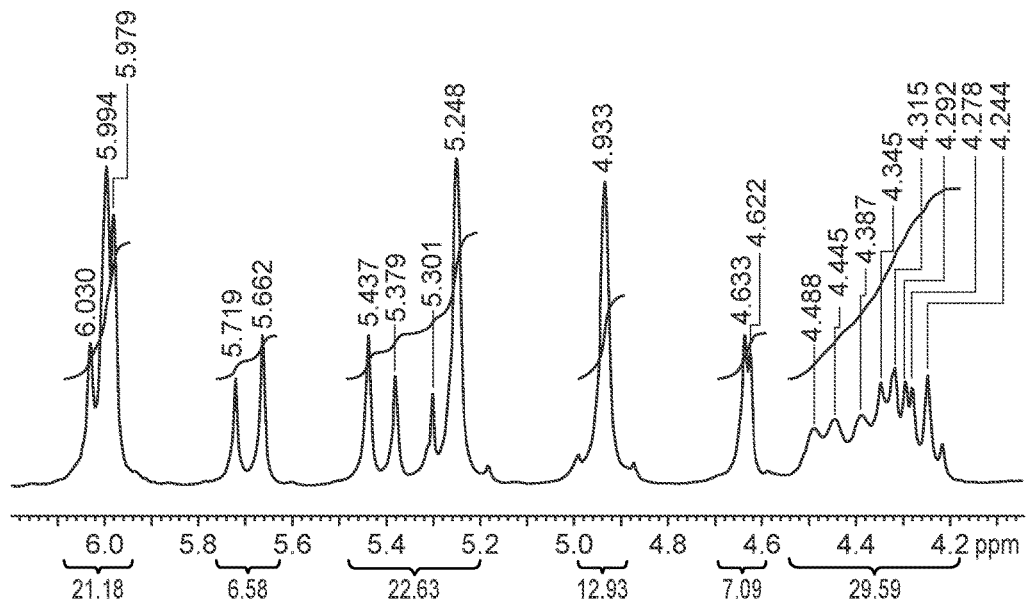
Figure 1E:
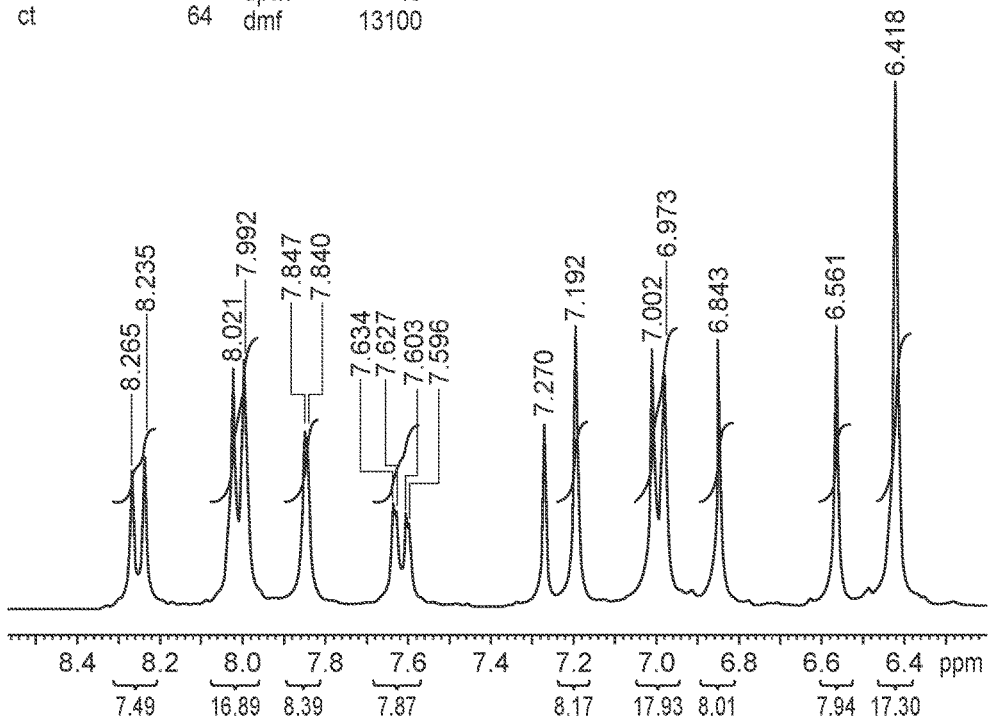
Figure 3B:
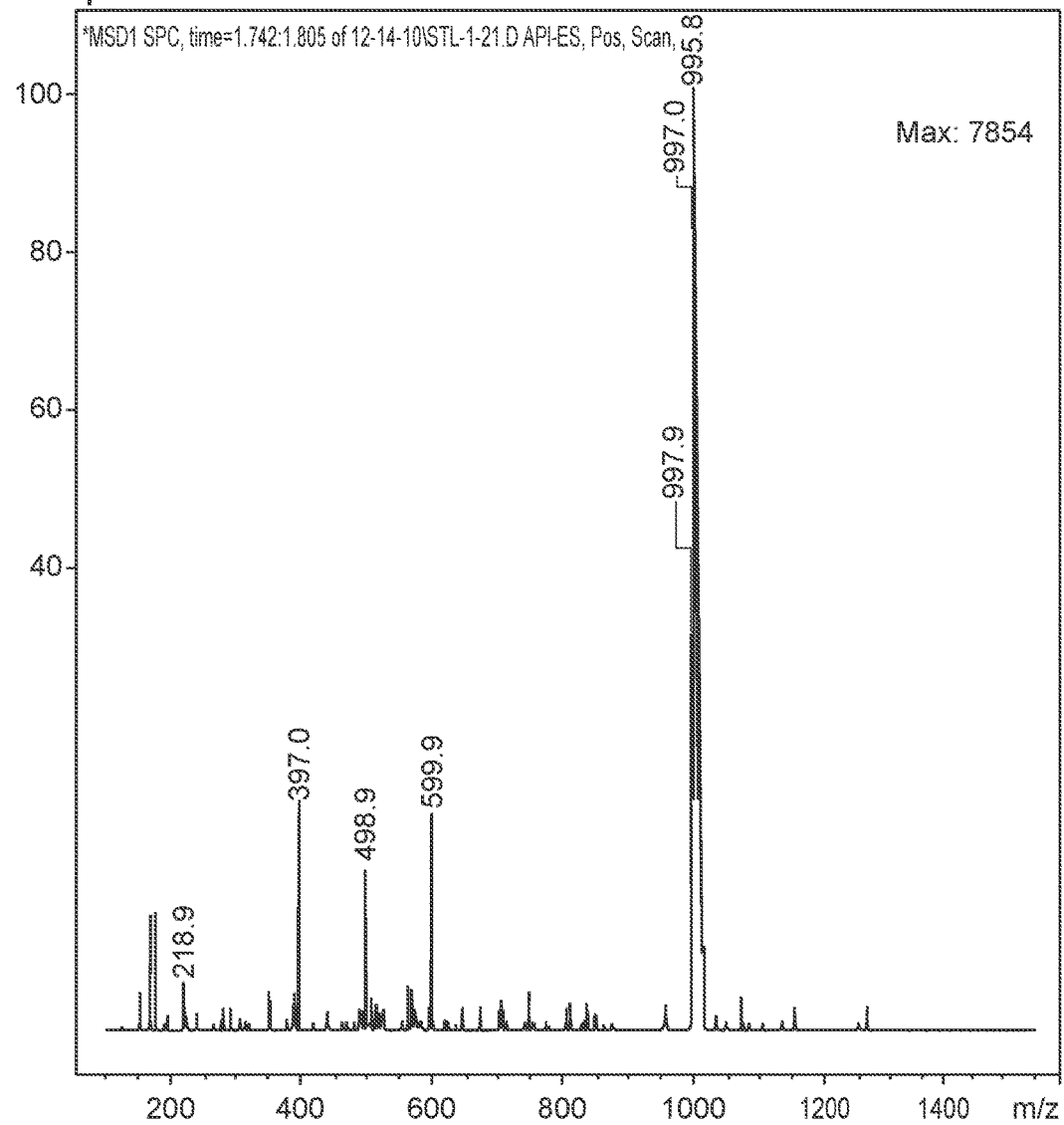
Figure 3C:
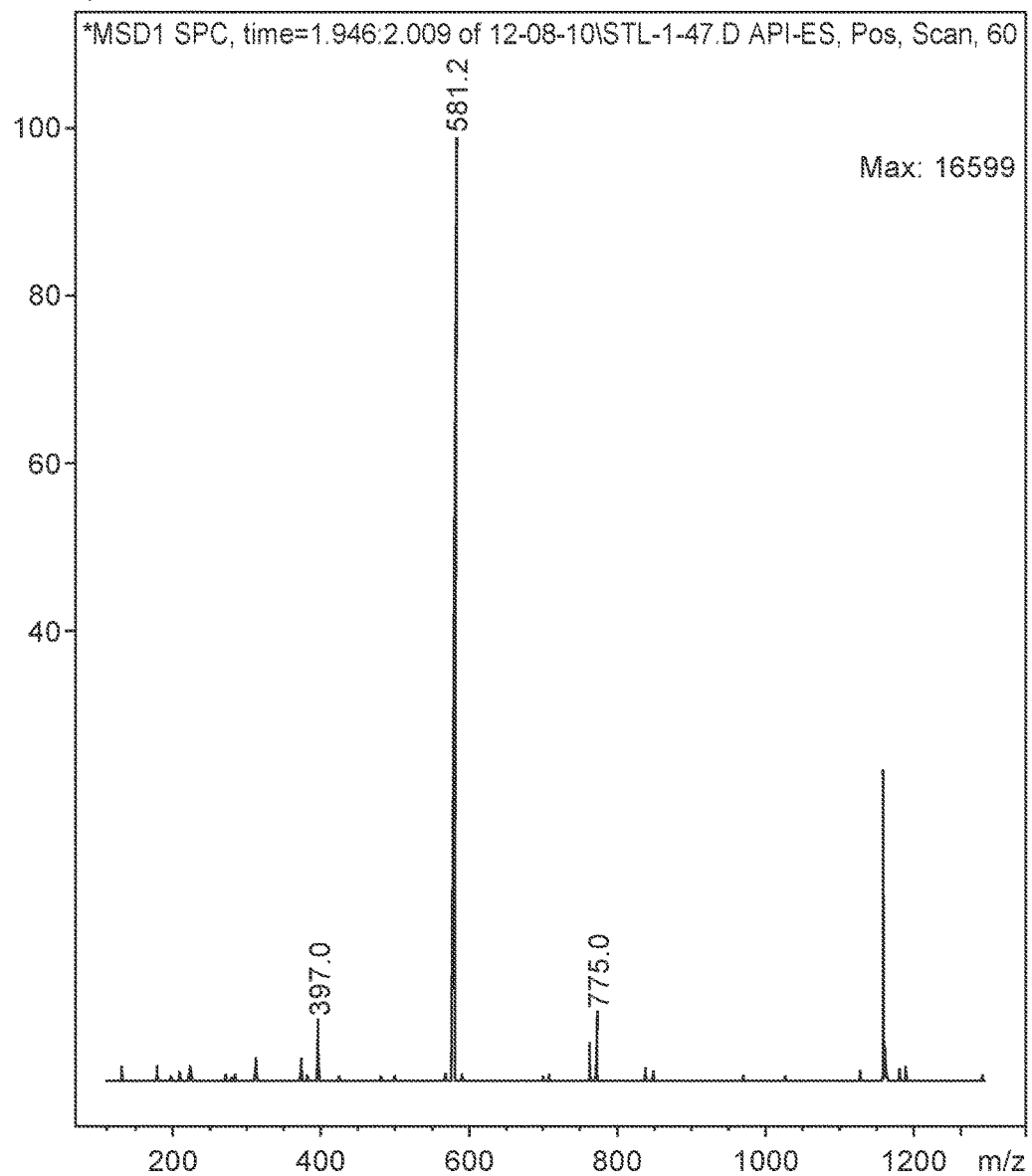

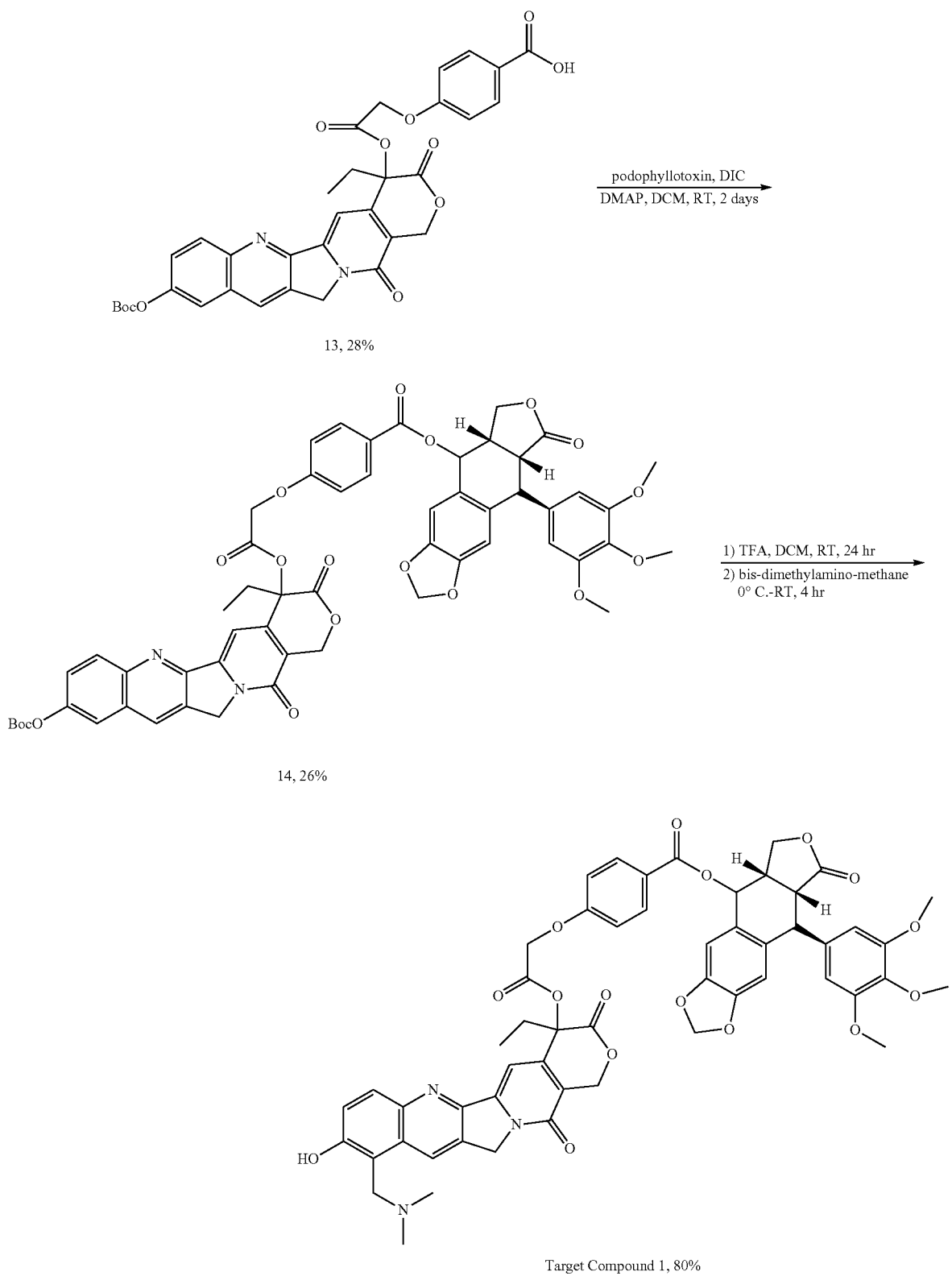
Target Compound 1, 80%
Target Compound 1 (also referred to herein as N1) can be synthesized following the procedures described above for N2 with any necessary modifications that will be apparent to a skilled artisan (see Scheme 6). The $^1$H NMR spectrum and LC-MS spectrum of Target Compound 1 are shown in FIGS. 1B and 3B respectively.

Example 5: Synthesis of Target Compound 3
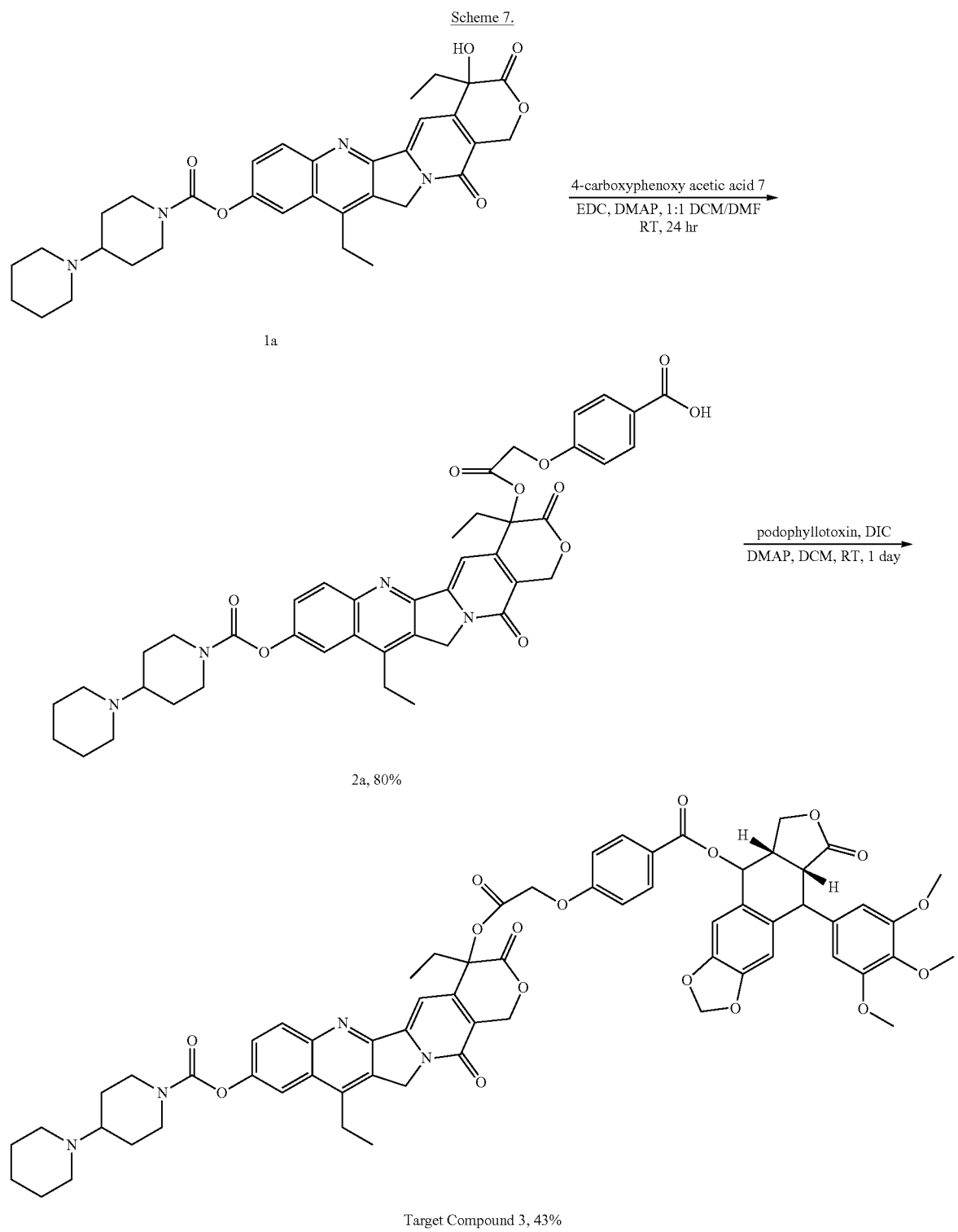
Target Compound 3 (also referred to herein as N3) can be synthesized following the procedures described above for N2 with any necessary modifications that will be apparent to a skilled artisan (see Scheme 7). The $^1$H NMR spectrum and LC-MS spectrum of Target Compound 3 are shown in FIGS. 1C-1E and 3C respectively.

Example 6: Synthesis of Target Compound 4
Scheme 8.
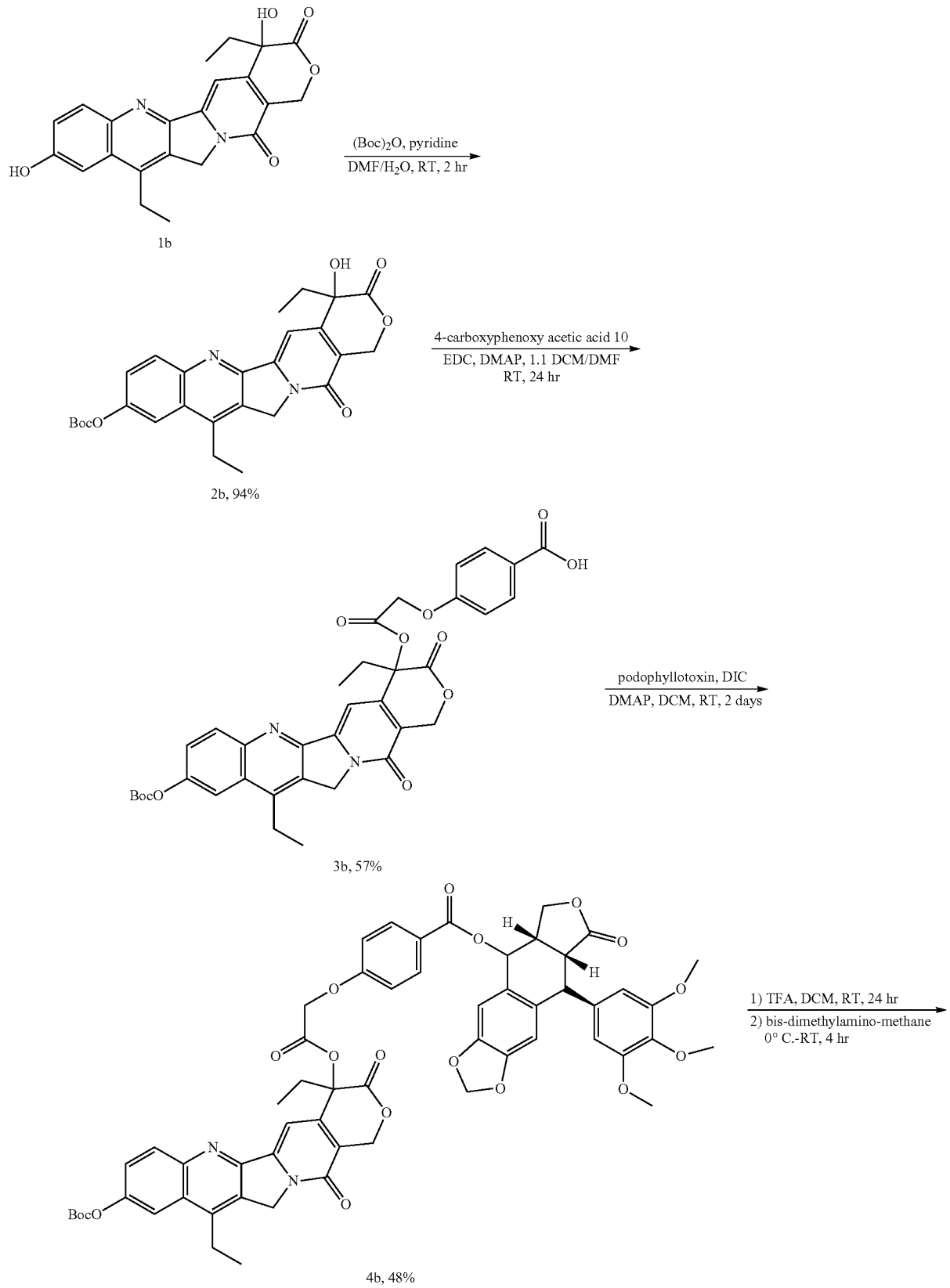

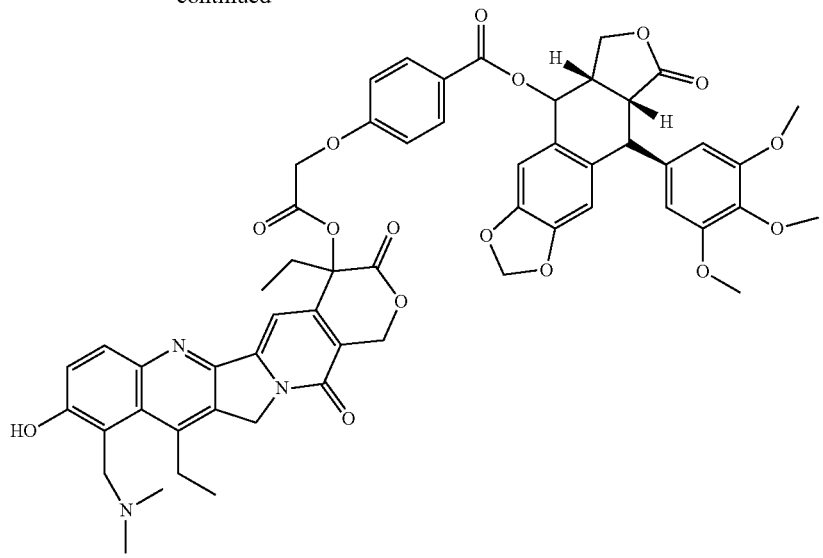

Target Compound 4, 56%

Figure 1F:
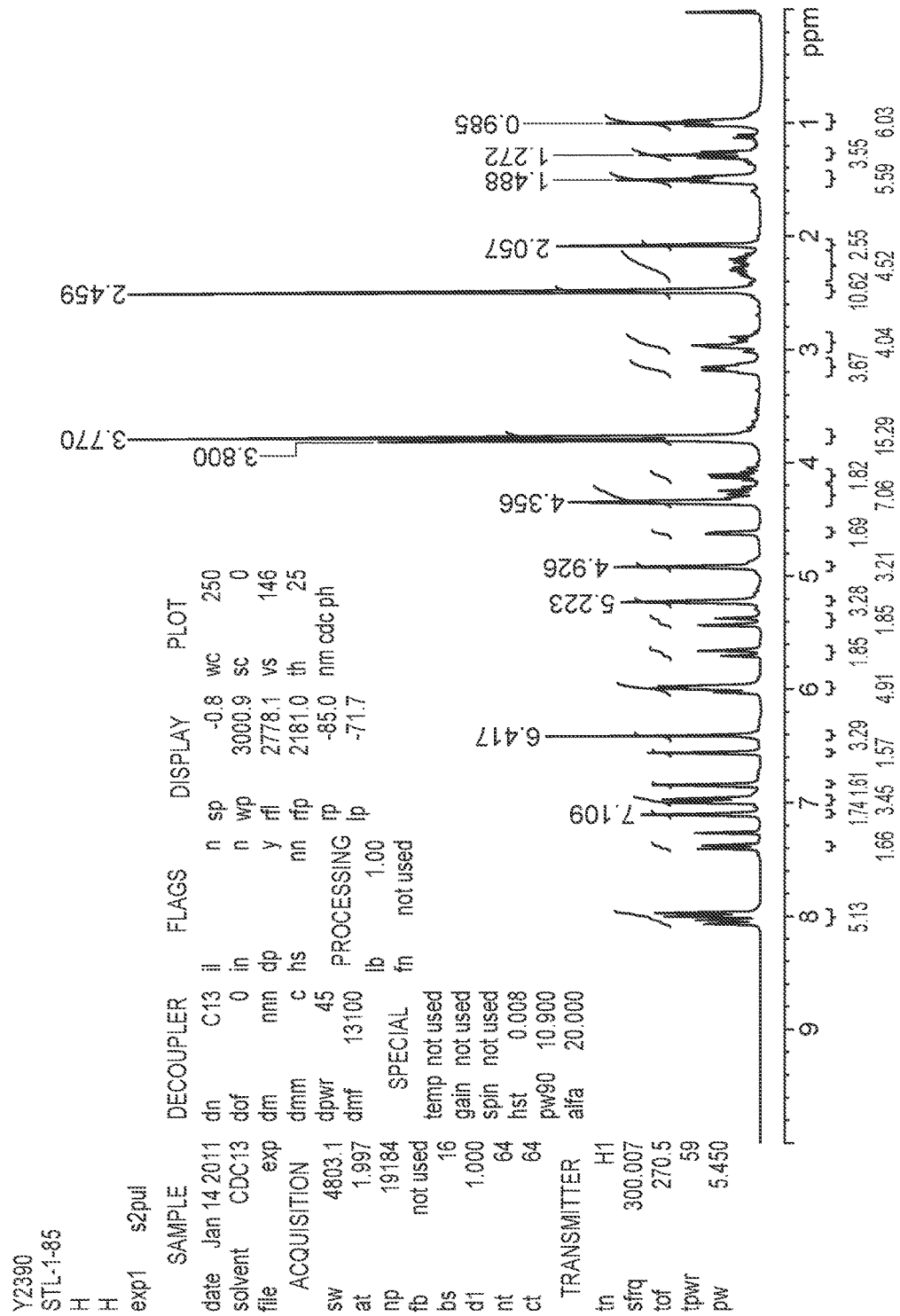
Figure 3D:
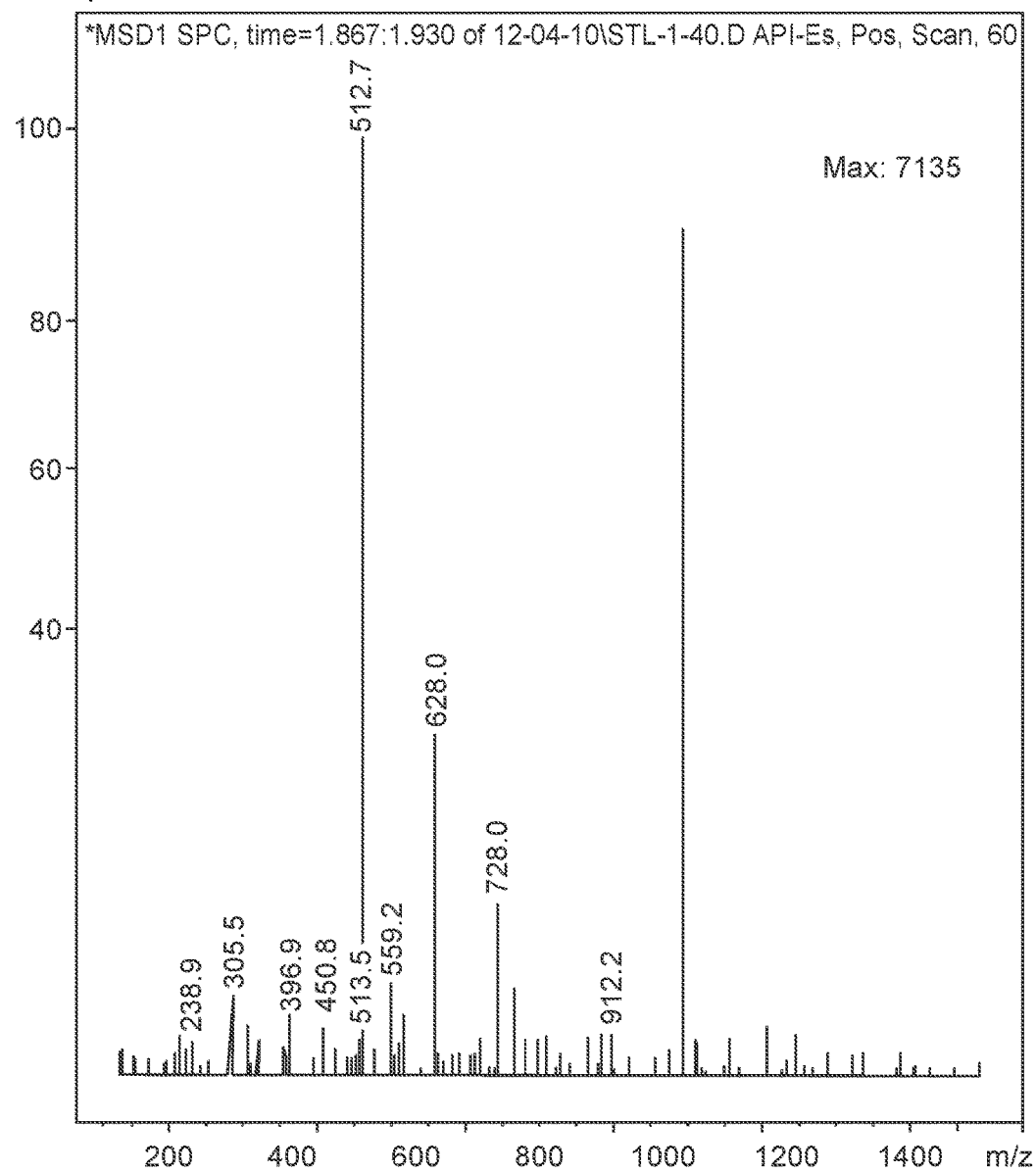

Target Compound 4 (also referred to herein as N4) can be synthesized following the procedures described above for N2 with any necessary modifications that will be apparent to a skilled artisan (see Scheme 8). The $^1$H NMR spectrum and LC-MS spectrum of Target Compound 4 are shown in FIGS. 1F and 3D respectively.

1.1. Background on Biological Assays

Studies were conducted using N2 and Target Compounds 1, 3, and 4. In vitro efficacy studies demonstrated that these compounds were very effective in killing human colon and lung cancer cells, and especially resistant colon cancer cells (overexpressing multi-drug resistant gene 1 [MDR1]). To further evaluate its preclinical efficacy, the in vivo efficacy studies have been conducted on two colon cancer models and one for Chronic Myeloid Leukemia (CML) model. The toxicity of four lead compounds were remarkably low in mice. Among them, N2 (also referred to herein as 801) is a promising compound with lower toxicity and higher efficacy against human cancer xenografts. The results showed that 801-HCl and formulated 801 are both effective for the human colon cancer and CML xenograft models.

1.2 In Vitro Efficacy Studies of Podophyllotoxin Analogs 1.2.1. Colony Formation Assay Cancer cells were plated in 60 mm Petri dishes containing 2.7 ml of medium (modified McCoy's 5a medium containing 10% fetal bovine serum and 100 units/ml penicillin and 100 ug/ml streptomycin). The cells were incubated in a $CO_2$ incubator at 37 degree C. for 5 hours for attachment to the bottom of Petri dishes. Drugs were made up fresh in medium at ten times the final concentration, and then 0.3 ml of this stock solution was added to the 2.7 ml of medium in the dish. The cells were then incubated with drugs for 72 hours at 37 degree C. At the end of incubation the drug-containing media were decanted, the dishes were rinsed with 4 ml of Hank's Balance Salt Solution (HBSS), 5 ml of fresh medium was added, and the dishes were returned to the incubator for colony formation. The cell colonies were counted using colony counter after incubation for 7 days (HCT116 cell line), 14 days (VM46 cell line) and 15 days (H23 cell line). Cell survival (%) was calculated from 3 repeated dishes for each drug concentration and the mean values of IC50 (the drug concentration producing 50% inhibition of colony formation) were determined for each tested compound.

1.2.2. Chemotherapeutic Effects on HCT116 Human Colon Cancer Cells

Chemotherapeutic Effects of podophyllotoxin Compounds (N1-4) on HCT116 Human Colon Cancer Cells are tabulated below.

| Compound | $IC_{50}$ (HCT116) |
| --- | --- |
| N1 | 24.2 nM |
| N2 (801) | above 500 nM |
| N3 | 282.7 nM |
| N4 | 6.6 nM |

1.2.3. Chemotherapeutic Effects on VM46 Human Colon Cancer Cells

Chemotherapeutic Effects of podophyllotoxin Compounds (N1-4) on VM46 Human Colon Cancer Cells Overexpressing Multi-drug Resistant Gene 1 are tabulated below.

| Compound | $IC_{50}$ (VM46) |
| --- | --- |
| N1 | 8 nM |
| N2 (801) | approximate 520 nM |
| N3 | 300 nM |
| N4 | 5 nM |

1.2.4. Chemotherapeutic Effects on H23 Human Non-Small Lung Cancer Cells

Chemotherapeutic Effects of podophyllotoxin Compounds (N1-4) on H23 Human Non-small Cell Lung Cancer Cells are tabulated below.

| Compound | $IC_{50}$ (H23) |
| --- | --- |
| N1 | 7.05 nM |
| N2 (801) | 461.76 nM |
| N3 | 200 nM |
| N4 | 12.94 nM |

In summary, N1, N2(801), N3, N4 all showed effectiveness against the 3 selected cell lines at nM level concentrations. N1 and N4 showed good effectiveness at very low concentration. Among the 3 cell lines, VM46 Human Colon Cancer Cells overexpress Multi-drug Resistant Gene 1 (MDR1). All compounds overcame MDR1 mediated drug resistance. N2(801) demonstrated more effectiveness against non-small cell lung cancer than colon cancer.

1.3. Toxicity Studies of Compounds N1-4 in Normal Mice
1.3.1. Method:

In the toxicity studies, 2 C3H female normal mice were dosed with compounds N1-4 (N1, N2, N3, and N4) at low and moderate doses of 40 and 100 mg/kg. Since no severe and irreversible toxicity occurred at these doses, a new pair of animals was initiated at 120 mg/kg which was 1.2 times higher than 100 mg/kg. Sequential dosages (ie. 2 mice for each drug dose) were increased by a factor of 1.2-1.5 until irreversible toxicity was observed (animal became emaciated; animal underwent rapid weight loss (cachexia) (20%) within several (2-4) days)(euthanasia was required) occurred. Then another pair of animals was initiated at the highest nontoxic dosage, and successive dosages were increased by a factor of 1.15. The result of this exercise were two dosages, one that was apparently nontoxic and the other that demonstrated irreversible toxicity that required euthanasia, separated by a factor of 1.15. Six mice were dosed at each dosage. If no irreversible toxicity occurred at the lower dosage and at least one with irreversible toxicity at the higher dose, then the lower dose was considered to be the MTD. HCL salts of N1-4 were formulated in a solution of ethanol:Cremophor EL:0.2M NaAc:saline (5:5:10:80) with a final pH of 5.0-5.5. N1-4 bases were formulated in a solution of ethanol: Cremophor EL:saline (5:5:90). All compounds were administered to C3H female normal mice by a single i.p. injection at a volume of 0.5 ml/20 g mouse. Drug toxicity was evaluated on mice checked daily for 40 days. The toxicity parameters reported were the $MTD_{40}$. The MTD was defined as the highest dose causing no irreversible toxicity in one treatment group, but at least one animal exhibiting irreversible toxicity and being euthanized at next higher dose. At the end of experiment, all mice were euthanized.

1.3.2. Results:

The evaluation of the toxic effects of N1, N2, N3, and N4 in C3H female normal mice have been completed. As shown in Table 1.3.1, the MTD values of all the compounds were significantly higher than many clinically available anticancer drugs. The higher its MTD, the lower its toxicity to normal mice. Among the four compounds, N2 was least toxic to normal mice. It is noted that the MTD of its base form was equal to that of its HCL salt form. The next less toxic one was Neovia4. Its base form was less toxic to mice than its HCL salt form, suggesting the less solubility of its base form might contribute to this difference.

TABLE 1.3.1

The MTD Values of Compounds N1-4 in C3H mice.

| Names of Compounds | MTD Values (mg/kg) |
| --- | --- |
| N1 HCL Salt | 120 |
| N2 Base | 300 |
| N2 HCL Salt | 300 |
| N3 HCL Salt | 144 |
| N4 Base | 250 |
| N4 HCL Salt | 180 |

1.4. Preliminary In Vivo Efficacy Study of Four Podophyllotoxin Analogs for Selection of the Most Promising Candidate Drug To evaluate in vivo efficacy of four compounds N1-4 on HCT116 human colon cancer, in vivo anticancer efficacy study was performed on nude mice (nu/nu genotype) bearing HCT116 human colon cancer xenografts.

1.4.1. Method

In vivo anticancer efficacy study was performed on nude mice (nu/nu genotype) bearing HCT116 human colon cancer xenografts. These human tumors grew exponentially following implantation into the flanks of the mice and reached an average tumor volume of 79.85 cu. mm. Treatment was initiated at that time, with the first day of treatment designated as day 0 for all calculations and plots. The 6 mice were injected i.p. with each of four Neovia drug solutions (5% alcohol, 5% Cremophor EL, and 90% saline, 0.5 ml/20 g, single injection). Drug doses (i.p. MTD doses) were 120 mg/kg for Neovia-1, 300 mg/kg for Neovia-2, 120 mg/kg for Neovia-3, and 180 mg/kg for Neovia-4. Control group of mice was treated with vehicle alone. After treatment, tumor sizes were measured by caliper every other day. The measurement of the tumor diameters (d1, d2) in two orthogonal directions was used to calculate the tumor volume (tumor volume=$\pi/6$ $\{(d1+d2)/2\}3$) using the approximation that the tumors are spherical. Each tumor growth curve for each mouse was plotted. The time (days) required to grow the tumor to the size of 800 cu. mm after various treatments was calculated as tumor growth delay indexes for evaluating the treatment effects. Survival times after treatment was also observed and recorded.

1.4.2. Results

All four compounds N1-4 after a single i.p. injection proved to be highly effective in inhibiting the growth of HCT116 human colon cancer xenografts. The results showed that N2 (801) would be the most promising candidate drug against HCT116 human colon cancer among all 4 compounds.

1.5. In Vivo Efficacy Study: 801 in Treatment of Subcutaneous COLO205 Human Colon Cancer Xenograft Model.

1.5.1. Objective

To evaluate preclinically the in vivo therapeutic efficacy and safety of compound 801 in the treatment of the subcutaneous COLO205 human colon cancer xenograft model and compared with the SOC drug irinotecan.

1.5.2. Animals

| Descriptor | Type |
| --- | --- |
| Species | *Mus Musculus* |
| Strain | BALB/c nude |
| Age | 6-8 weeks |
| Sex | Female |
| Body weight | 18-22 g |
| Number of animals | 40 mice |
| Animal supplier | Beijing Vital River Inc |

1.5.3. Method

Each mouse was inoculated subcutaneously with $5\times10^6$ COLO205 tumor cells in 0.1 ml PBS for tumor development. Treatments were started when the tumor volume reached 120 $mm^3$. The major endpoint was to see if the tumor growth could be delayed or regressed. Body weight and tumor volume were measured twice a week. Tumor volume was then used for calculations of both T-C and tumor growth inhibition (TGI) values.

1.5.4. Groups and Treatments

| Group | Treatment (Vehicle) | Number of animals | Dosage (mg/kg) | Route/ schedule | Dosing Volume | Number of Injections |
|---|---|---|---|---|---|---|
| 1 | Vehicle: mPEG-2000-DSPE | 8 | — | i.v., q5d x 3 | 46.81 µl/g BW (13.33 mg/ml) | 4 injections, 1.5 hrs interval |
| 2 | mPEG-2000-DSPE formulated 801 | 8 | 125 | i.v., q5d x 3 | 46.81 µl/g BW | 4 injections, 1.5 hrs interval |
| 3 | mPEG-2000-DSPE formulated 801 | 8 | 100 | i.v., q3d x 3 | 37.45 µl/g BW | 3 injections, 1. hrs interval |
| 4 | 801-HCl | 8 | 125 | i.p., q3d x 3 | 10 µl/g BW, | one bolus |
| 5 | Irinotecan | 8 | 70 | i.p., q3d x 3 | | |

1.5.5. Statistics

The differences between the mean values of tumor volume for comparing groups were analyzed for significance using the one-way ANOVA test. $P<0.05$ was considered as statistically significant.

1.5.6. Results

The results from show i.v. mPEG-2000-DSPE formulated 801 at dose levels of 125 mg/kg (q5dx3) and 100 mg/kg (q3dx3) produced a moderate antitumor activity with TGI values of 37% and 42%, respectively ($p=0.008$ and $p=0.002$ vs. control).

The results show i.p. 801-HCl at 125 mg/kg and irinotecan at 70 mg/kg produced a strong antitumor activity with TGI values of 70% and 97% at day 29 (both $p<0.001$ vs. control).

Figure 4B:
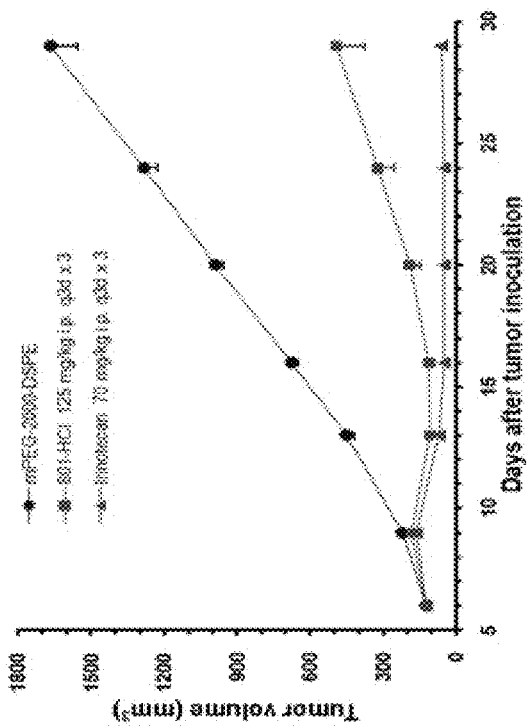
FIG. 4B shows the antitumor activity of N2-HCl (i.p.) in treatment of COLO205 Human Colon Cancer Xenograft Model.
Figure 4A:
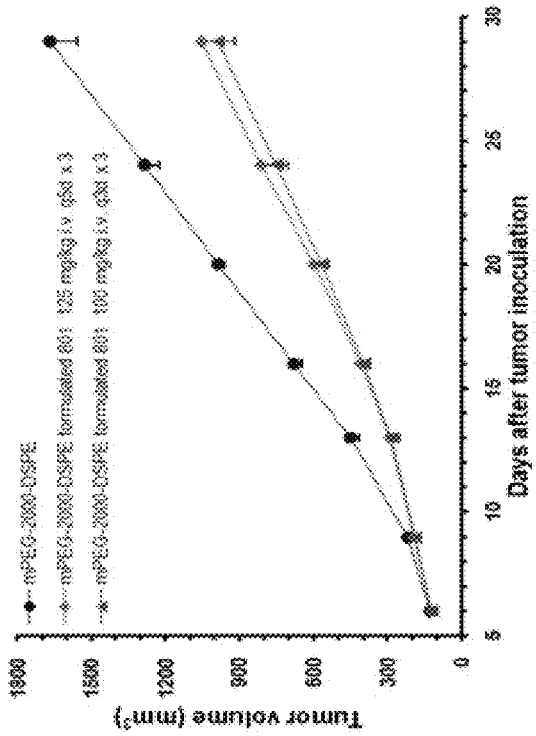
FIG. 4A shows the antitumor activity of formulated N2-HCl (i.v.) in treatment of COLO205 Human Colon Cancer Xenograft Model.

FIG. 4A shows the antitumor activity of formulated N2-HCl (i.v.) in treatment of COLO205 Human Colon Cancer Xenograft Model and FIG. 4B shows the antitumor activity of formulated N2-HCl (i.p.) in treatment of COLO205 Human Colon Cancer Xenograft Model.

Regarding the safety profile, the mice tolerated the treatments well; no severe body weight loss or other gross clinical abnormalities were observed during the treatment period.

1.5.7. Conclusion

801-HCl at 125 mg/kg (i.p. delivery) demonstrated a strong antitumor activity with a good safety profile. mPEG-2000-DSPE formulated 801 (i.v. delivery) produced a moderate efficacy, which might be caused either by a splited injections for each i.v. dosing due to a limitation in dosing volume allowance for i.v. injection in mice.

1.6. In-Vivo Efficacy Study: 801 in Treatment of Subcutaneous HCT116 Human Colon Cancer Xenograft Model

1.6.1. Objective

To evaluate preclinically the in vivo therapeutic efficacy and safety of compound 801 in the treatment of the subcutaneous HCT116 human colon cancer xenograft model in nude mice.

1.6.2. Animals

| Descriptor | Type |
|---|---|
| Species | *Mus Musculus* |
| Strain | BALB/c nude |
| Age | 6-8 weeks |
| Sex | Female |
| Body weight | 18-22 g |
| Number of animals | 40 mice |
| Animal supplier | Beijing Vital River Inc |

1.6.3. Method

Each mouse was inoculated subcutaneously with $5\times10^6$ HCT116 tumor cells in 0.1 ml PBS for tumor development. Treatments were started when the tumor volume reached 100 mm³. The major endpoint was to see if the tumor growth could be delayed or regressed. Body weight and tumor volume were measured twice a week. Tumor volume was then used for calculations of both T-C and tumor growth inhibition (TGI) values.

1.6.4. Groups and Treatments

| Group | Treatment (Vehicle) | Number of animals | Dosage (mg/kg) | Route/ schedule | Dosing Volume | Number of Injections |
|---|---|---|---|---|---|---|
| 1 | Vehicle: mPEG-2000-DSPE | 8 | — | i.v., q5d x 3 | 46.81 µl/g BW (13.33 mg/ml) | 4 injections, 1.5 hrs interval |
| 2 | mPEG-2000-DSPE formulated 801 | 8 | 125 | i.v., q5d x 3 | 46.81 µl/g BW | 4 injections, 1.5 hrs interval |
| 3 | mPEG-2000-DSPE formulated 801 | 8 | 100 | i.v., q3d x 3 | 37.45 µl/g BW | 3 injections, 1. hrs interval |
| 4 | 801-HCl | 8 | 125 | i.p., q3d x 3 | 10 µl/g BW, | one bolus |
| 5 | Irinotecan | 8 | 70 | i.p., q3d x 3 | | |

1.6.5. Statistics

The differences between the mean values of tumor volume for comparing groups were analyzed for significance using the one-way ANOVA test. $P<0.05$ was considered as statistically significant.

1.6.6. Results

Figure 5B:
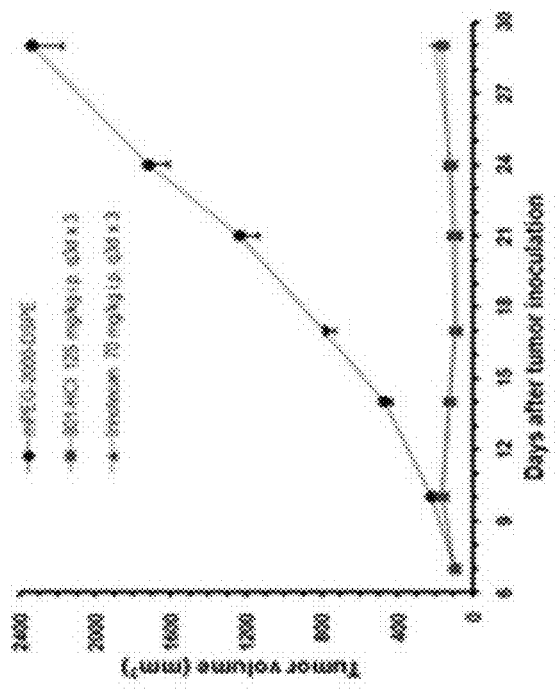
FIG. 5B shows the antitumor activity of N2-HCl (i.p.) in treatment of HCT116 Human Colon Cancer Xenograft Model.
Figure 5A:
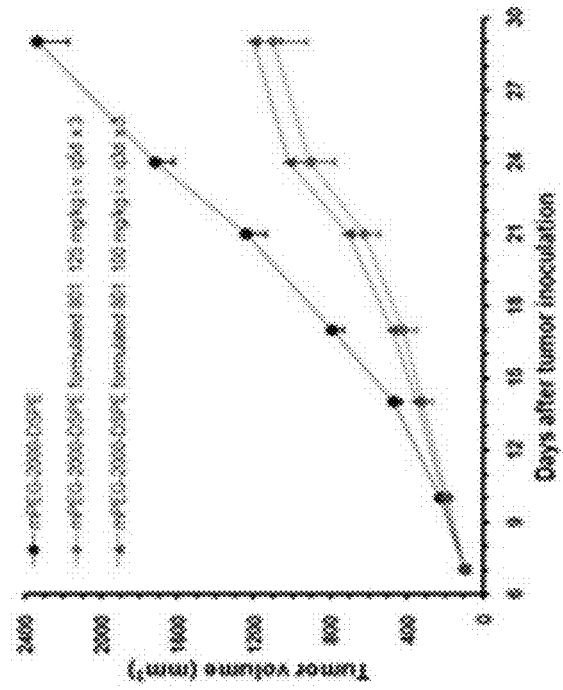
FIG. 5A shows the antitumor activity of formulated N2 (i.v.) in treatment of HCT116 Human Colon Cancer Xenograft Model.

The results from FIG. 5A show i.v. mPEG-2000-DSPE formulated 801 at dose levels of 125 mg/kg (q5dx3) and 100 mg/kg (q3dx3) produced a moderate antitumor activity with TGI values of 52% and 49%, respectively ($p=0.002$ and $p=0.001$ vs. control).

The results from FIG. 5B show i.p. 801-HCl at 125 mg/kg and irinotecan at 70 mg/kg produced a similar and strong antitumor activity with TGI values of 93% and 92% at day 29 (both p<0.001 vs. control).

FIG. 5A shows the antitumor activity of formulated N2 (i.v.) in treatment of HCT116 Human Colon Cancer Xenograft Model. FIG. 5B shows the antitumor activity of N2-HCl (i.p.) in treatment of HCT116 Human Colon Cancer Xenograft Model.

Regarding the safety profile, a minor body weight loss (4-6%) was observed for 801-HCl and formulated 801 treated animals, while irinotecan resulted in 8% body weight loss. No other gross clinical abnormalities were observed during the treatment period.

1.6.7. Conclusion

801-HCl at 125 mg/kg (i.p.) demonstrated a strong antitumor activity with a good safety profile. mPEG-2000-DSPE formulated 801 (i.v.) produced a moderate efficacy, which might be caused either by splited injections for daily iv dosing due to a limitation in volume allowance for iv injection in mice.

1.7. In Vivo Efficacy Study: 801 in Treatment of Subcutaneous K562 Human Chronic Myeloid Leukemia Xenograft Model.

1.7.1. Objectives

Preclinically evaluate in vivo therapeutic efficacy and safety of compound 801 in the treatment of the subcutaneous human chronic myeloid leukemia xenograft model in NOD/SCID mice.

1.7.2. Animals

| Descriptor | Type |
| --- | --- |
| Species | *Mus Musculus* |
| Strain | NOD/SCID |
| Age | 6-8 weeks |
| Sex | Female |
| Body weight | 22-26 g |
| Number of animals | 32 mice |
| Animal supplier | Beijing HFK Bio-Technology Co., Ltd. |

1.7.3. Method

The mice were irradiated (2Gy) using a Co60 irradiator source. After 24 hours, each animal was inoculated subcutaneously on the right flank with K562 cells ($1\times10^7$/animal) in 0.1 mL of PBS for tumor development. Tumor development was allowed undisrupted until the mean volume reached approximately 150 mm$^3$. The major endpoint was to see if the tumor growth could be delayed or regressed. Body weight and tumor volume were measured. Tumor volume was then used for calculations of both T-C and tumor growth inhibition (TGI) values.

1.7.4. Groups and Treatments

TABLE 1.7

| Group | Number of animals | Treatment | Dose (mg/kg) | Route of administration | Days of Treatment | Dose Volume |
| --- | --- | --- | --- | --- | --- | --- |
| 1 | 8 | Vehicle: mPEG-2000-DSPE | same as Group 2. | iv | TID on Days 8, 11, 14 | |
| 2 | 8 | mPEG-2000-DSPE formulated 801 | 60 | iv | TID on Day 8 | 20 µl/g |
| 3 | 8 | 801-HCl | 300 | ip | Days 8, 11, 14 | 20 µl/g |
| 4 | 8 | Imatinib mesylate | 75 | po | Days 8-21 | 10 µl/g. |

1.7.5. Statistics

The differences between the mean tumor volumes of comparing groups were analyzed for statistical significance using one-way ANOVA test. P<0.05 was considered as statistically significant.

1.7.6. Results

The control animals were euthanized on Day 25 for large tumor burden.

The mPEG-2000-DSPE vehicle was tolerated well by the control animals. However, the mPEG-2000-DSPE formulated 801 at the test dosage of 60 mg/kg (iv, TID dosing) caused severe toxicity to the animals and only one TID dosing was delivered; a drastic BW loss of 14.5% was observed on the next day after the Day 8 dosing, with 2 out of 8 animals died on Days 9 and 10. The test agent 801-HCl was tolerated well by the animals when delivered ip at a dosage of at 300 mg/kg, with only a maximum 7.7% BW loss recorded on the next day after the 2nd dosing. The positive drug imatinib was tolerated well by the animals, and a minor BW loss of 6.2% was observed at the end of the treatment.

Figure 6:
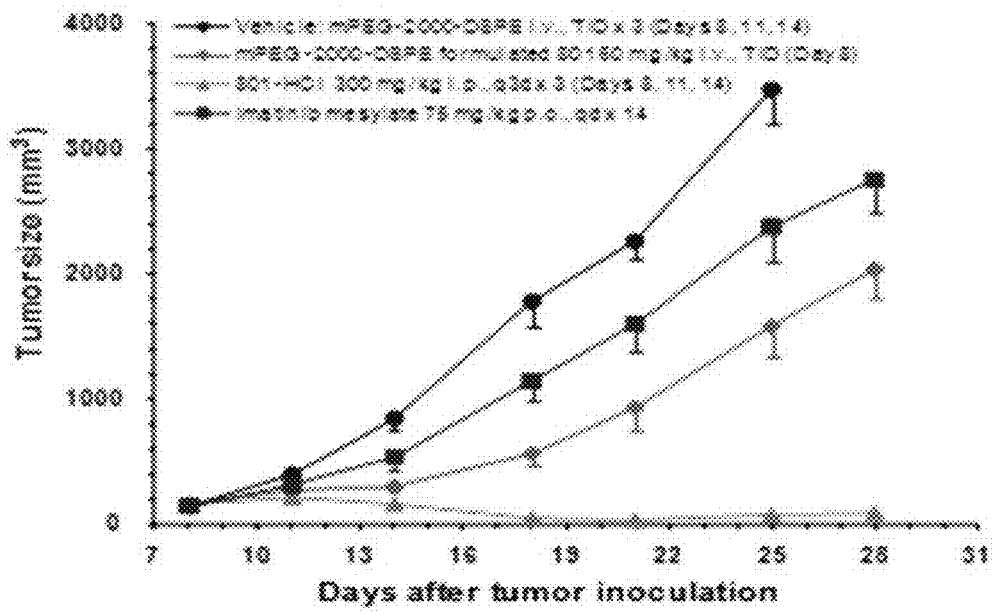
FIG. 6 shows the tumor growth curves of the different groups of mice described in Table 1.7.

The mean TVs of different groups are presented in Table 1.7.1. The TGI values on Day 25 are shown in Table 1.7.2. The tumor growth curves of the different mice groups tabulated in Table 1.7 are presented in FIG. 6.

The mean TV of control animals reached 3,467 mm$^3$ on Day 25 after the tumor cell inoculation. Test agent mPEG-2000-DSPE formulated 801 (60 mg/kg, iv, TID: total 180 mg/kg), administered for only one-day due to tolerability issue, still produced moderate antitumor activity with a TGI value of 55% (p=0.001 vs. control). Test agent 801-HCl at 300 mg/kg (ip) exhibited a drastic antitumor activity with a TGI value of 98% (p<0.001 vs. control). For this treatment group, 3 out 8 animals achieved complete remission of the tumors by Day 21 (7 days after the last dosing) without further tumor regrowth by the end of the study. In comparison, imatinib at 75 mg/kg(po) exhibited only minor antitumor activity with a TGI value of 33%, which is not significant from the control (p=0.064 vs. control).

TABLE 1.7.1

Mean Tumor Volumes.

| | Mean Tumor Volume (mm$^3$) | | | |
| --- | --- | --- | --- | --- |
| Days[1] | Vehicle mPEG-2000-DSPE | mPEG-2000-DSPE formulated 801 60 mg/kg, TID on Day 8 | 801-HCl 300 mg/kg, Days 8, 11, 14 | Imatinib mesylate 75 mg/kg, Days 8-21 |
| 8 | 156 ± 12 | 159 ± 9 | 159 ± 16 | 156 ± 12 |
| 11 | 403 ± 52 | 276 ± 23 | 221 ± 27 | 324 ± 57 |
| 14 | 851 ± 83 | 300 ± 29 | 164 ± 16 | 545 ± 105 |

TABLE 1.7.1-continued

Mean Tumor Volumes.

| | Mean Tumor Volume (mm³) | | | |
|---|---|---|---|---|
| Days[1] | Vehicle mPEG-2000- DSPE | mPEG-2000- DSPE formulated 801 60 mg/kg, TID on Day 8 | 801-HCl 300 mg/kg, Days 8, 11, 14 | Imatinib mesylate 75 mg/kg, Days 8-21 |
| 18 | 1,778 ± 206 | 576 ± 97 | 47 ± 7 | 1,146 ± 152 |
| 21 | 2,259 ± 150 | 933 ± 178 | 39 ± 6 | 1,596 ± 210 |
| 25[2] | 3,467 ± 270 | 1,581 ± 245 | 74 ± 12 | 2,368 ± 268 |
| 28 | — | 2,032 ± 231 | 95 ± 19 | 2,761 ± 283 |

Values are presented as mean ± standard error.
[1]Days after tumor inoculation.
[2]The control group was terminated on Day 25 for large tumor burden.

TABLE 1.7.2

Antitumor Activity of 801 in Treatment of the Subcutaneous K562 Human Chronic Myeloid Leukemia Model.

| Groups | Mean TVs (mm³, D25) | P values[1] Dunnett T3 test | TGI (Day 25[2]) | CR ratio[3] |
|---|---|---|---|---|
| G1: Vehicle mPEG-2000-DSPE | 3,467 ± 270 | — | — | — |
| G2: mPEG-2000-DSPE formulated 801 | 1,581 ± 245 | 0.001 | 55 | — |
| G3: 801-HCl | 74 ± 12 | <0.001 | 98 | 3/8 |
| G4: Imatinib mesylate | 2,368 ± 268 | 0.064 | 33 | — |

TGI = Tumor growth inhibition.
[1]vs. G1: Vehicle on Day 25.
[2]Days after tumor inoculation.
[3]The ratio of complete regression.
Other comparisons: G2 vs. G3, p = 0.007; G2 vs. G4, p = 0.244; G3 vs. G4, p < 0.001.

1.7.7. Conclusion

801-HCl at 300 mg/kg (i.p.) exhibited a drastic antitumor activity with a good safety profile. mPEG-2000-DSPE formulated 801 (60 mg/kg, iv, TID: total 180 mg/kg), administered for only one-day due to tolerability in the mice irradiated at 2Gy using a Co60 irradiator source, still produced moderate antitumor activity.

1.8. In Vivo Efficacy Study: 801 in Treatment of K562 Human Chronic Myeloid Leukemia Xenograft Model (2$^{nd}$ K562 Study).

1.8.1. Objectives

The objective of this study was to evaluate preclinically in vivo therapeutic efficacy and tolerability of the test article, compound 801, in treatment of the subcutaneous K562 human chronic myeloid leukemia xenograft in NOD SCID mice, and compared with these of SOC drug imatinib.

1.8.2. Animals

| Descriptor | Type |
|---|---|
| Species | *Mus Musculus* |
| Strain | NOD/SCID |
| Age | 6-8 weeks |
| Sex | Female |
| Body weight | 18-22 g |
| Number of animals | 48 mice plus spare |
| Animal supplier | Beijing Vital River Inc., Beijing, China |

1.8.3. Method

The mice were irradiated (200 rad) using a Co60 irradiator source. After 24 hours, each animal was inoculated subcutaneously on the right flank with K562 cells (1×107/animal) in 0.1 mL of PBS for tumor development. Tumor development was allowed undisrupted until the mean volume reached approximately 130 mm3. Animals were then randomized into 6 groups, with each group consisting of 8 animals. The test articles were administered to the tumor-bearing animals according to predetermined regimens as shown in the experiment design table above.

1.8.4. Groups and Treatments

TABLE 1.8

| Group | n | Treatment | Dose (mg/kg) | ROA | schedule |
|---|---|---|---|---|---|
| 1 | 8 | Vehicle: mPEG-2000-DSPE | — | i.v. | q3d × 2 (bid injection) q3d × 4 (qd injection) |
| 2 | 8 | Imatinib | 75 | p.o. | qd × 14 |
| 3 | 8 | mPEG-2000-DSPE formulated 801 | 150 | i.v. | q3d × 2 (tid injection) |
| 4 | 8 | mPEG-2000-DSPE formulated 801 | 100 | i.v. | q3d × 2 (bid injection) |
| 5 | 8 | mPEG-2000-DSPE formulated 801 | 50 | i.v. | q3d × 8 (qd injection) |
| 6 | 8 | mPEG-2000-DSPE formulated 801 | 25 | i.v. | q3d × 8 (qd injection) | n = number of animals;
ROA = route of administration;
i.v. = intravenously;
p.o. = per os (orally).
Dosing volume for formulated 801 and the vehicle control was 20 µl/g based on body weight, the dosing volume for Imatinib solution was 10 µl/g.

1.8.5. Statistics

The differences between the mean tumor volumes of comparing groups were analyzed for statistical significance using one-way ANOVA test. P<0.05 was considered as statistically significant.

1.8.6. Results a. 1.8.6.1 Tumor Volumes

The tumor sizes of the different groups are shown in Table 1.8.1.

TABLE 1.8.1

Tumor Sizes in the Treatment Groups

| | Mean Tumor Volume (mm³)[1] | | | | | |
|---|---|---|---|---|---|---|
| Days[2] | Vehicle: mPEG-2000- DSPE i.v. q3d × 6 | Imatinib mesylate 75 mg/kg p.o. qd × 14 | Formulated 801 150 mg/kg i.v. q3d × 2 | Formulated 801 100 mg/kg i.v. q3d × 2 | Formulated 801 50 mg/kg i.v. q3d × 8 | Formulated 801 25 mg/kg i.v. q3d × 8 |
| 8 | 130 ± 9 | 129 ± 10 | 129 ± 10 | 128 ± 7 | 127 ± 9 | 129 ± 7 |
| 11 | 324 ± 29 | 206 ± 32 | 135 ± 14 | 138 ± 16 | 185 ± 16 | 192 ± 15 |
| 14 | 607 ± 71 | 423 ± 75 | 163 ± 15 | 221 ± 29 | 260 ± 29 | 354 ± 26 |

TABLE 1.8.1-continued

Tumor Sizes in the Treatment Groups

| | Mean Tumor Volume (mm³)[1] | | | | | |
|---|---|---|---|---|---|---|
| Days[2] | Vehicle: mPEG-2000-DSPE i.v. q3d x 6 | Imatinib mesylate 75 mg/kg p.o. qd x 14 | Formulated 801 150 mg/kg i.v. q3d x 2 | Formulated 801 100 mg/kg i.v. q3d x 2 | Formulated 801 50 mg/kg i.v. q3d x 8 | Formulated 801 25 mg/kg i.v. q3d x 8 |
| 18 | 1,290 ± 81 | 765 ± 121 | 338 ± 47 | 453 ± 58 | 474 ± 57 | 666 ± 48 |
| 21 | 1,643 ± 95 | 1,094 ± 123 | 639 ± 81 | 826 ± 85 | 585 ± 59 | 936 ± 89 |
| 25[3] | 2,401 ± 167 | 1,504 ± 120 | 1,013 ± 105 | 1,222 ± 107 | 776 ± 69 | 1,305 ± 147 |
| 28 | — | 2,058 ± 168 | 1,514 ± 146 | 1,589 ± 109 | 1,007 ± 134 | 1,556 ± 180 |
| 32 | — | 2,676 ± 236 | 2,213 ± 247 | 2,321 ± 193 | 1,435 ± 133 | 1,976 ± 216 |

[1]Values are presented as Mean ± SEM
[2]Days after tumor inoculation.
[3]The control group was terminated on Day 25 for large tumor burden.

b. 1.8.6.2 Tumor Growth Inhibition

Figure 7:
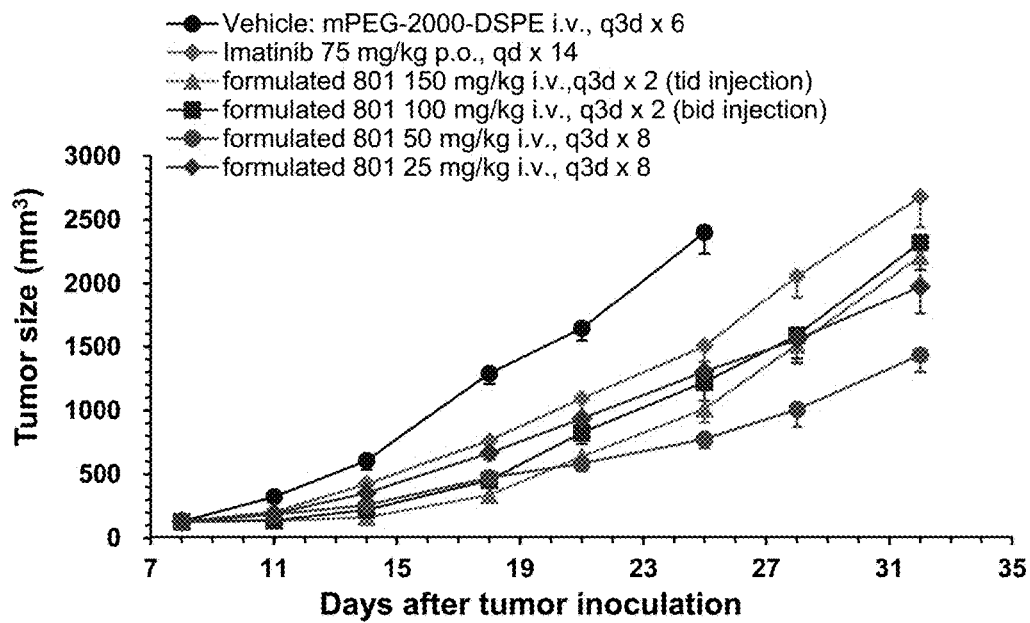
FIG. 7 shows the antitumor activity of formulated N2 and Imatinib in the treatment of K562 Xenograft Model.

The tumor growth inhibition was summarized in Table 1.8.2. The tumor growth curves of different mice groups treated with formulated 801 and imatinib as tabulated in Table 1.8 are presented in FIG. 7.

TABLE 1.8.2

Antitumor Activity of formulated 801 and Imatinib in the Treatment of the K562 Human Chronic Myeloid Leukemia Xenograft Model

| Treatment | Tumor Size (D25, mm³)[1] | TGI (%) | P value[2] |
|---|---|---|---|
| G1: Vehicle Control | 2,401 ± 167 | — | — |
| G2: Imatinib mesylate 75 mg/kg | 1,504 ± 120 | 37 | <0.001 |
| G3: Formulated 801 150 mg/kg | 1,013 ± 105 | 62 | <0.001 |
| G4: Formulated 801 100 mg/kg | 1,222 ± 107 | 51 | <0.001 |
| G5: Formulated 801 50 mg/kg | 776 ± 69 | 70 | <0.001 |
| G6: Formulated 801 25 mg/kg | 1,305 ± 147 | 45 | <0.001 |

[1]Values are presented as Mean ± SEM
[2]vs. vehicle control;
P values: G2 vs G3 = 0.013; G2 vs G4 = 0.144; G2 vs G5 <0.001; G2 vs G6 = 0.262; G3 vs G4 = 0.305; G3 vs G5 = 0.248; G3 vs G6 = 0.130; G4 vs G5 = 0.033; G4 vs G6 = 0.665; G5 vs G6 = 0.008;

1.8.7 Conclusion

Formulated 801 at the dose of 50 mg/kg with q3d×8 treatment schedule demonstrated a strong antitumor activity in K562 human chronic myeloid leukemia xenograft model, but under the toxicity. The dose of 50 mg/kg was significantly more effective against K562 CML xenografts than the dose of 25 mg/kg using the same treatment schedule, revealing a dose-response relationship. Formulated 801 at dose level (50 mg/kg) showed significantly the stronger antitumor activity than that of imatinib (p<0.001).

2.0 Safety Studies

The toxicity studies in normal Cynomolgus monkeys showed that after dosing with 801 HCl via intravenous infusion twice daily with a 5-hour interval, the MTD was the 60 mg/kg/day. The results of a 5-day repeat dose toxicity study of 801 HCl following intravenous infusion in Cynomolgus Monkeys exhibited the MTD of 801 was 30 mg/kg/day for repeating dosing.

In the rat MTD study, Sprague-Dawley rats were dosed with 801 HCl at a concentration of 6 mg/ml via intravenous infusion or slow intravenous injection. The MTD of 801 in normal rats was 120 mg/kg/day. In the 7-day repeating dose study, the rats were administered with 891 via BID slow IV injection for 7 days. The data showed that the MTD of 801 was 60 mg/kg/day for repeating doing.

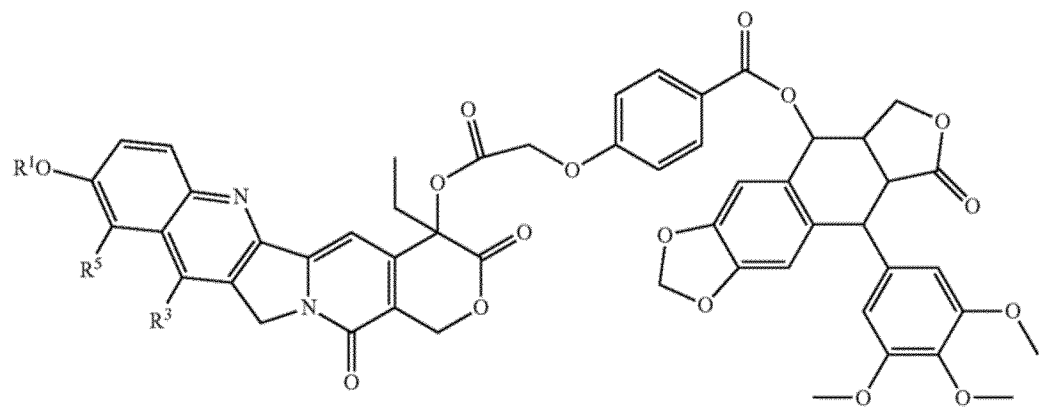

The invention claimed is:

1. A compound of formula (I):

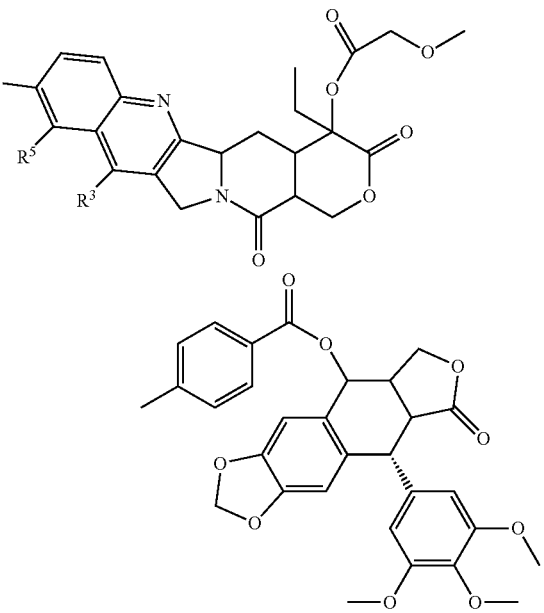

or an N-oxide thereof, or a pharmaceutically acceptable salt of each thereof, or a pharmaceutically acceptable solvate of each of the foregoing, wherein $R^1$ is H or has a structure of:

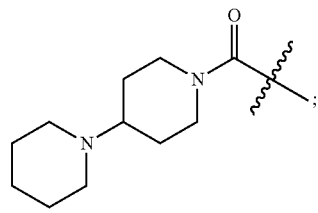 [SMILES: *C(=O)N1CCC(N2CCCCC2)CC1]

$R^3$ is H, an optionally substituted $C_1$-$C_8$ alkyl, an optionally substituted 3-10 membered cycloalkyl, an optionally substituted 3-10 membered heterocyclyl, an optionally substituted 6-10 membered aryl, or an optionally substituted 5-10 membered heteroaryl;

$R^5$ is H or has a structure of:

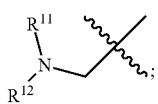

and $R^{11}$ and $R^{12}$ independently is an optionally substituted $C_1$-$C_8$ alkyl.

2. The compound of claim 1, wherein $R^1$ is H.

3. The compound of claim 1, wherein $R^1$ has the structure of:

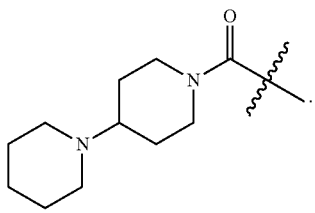 [SMILES: *C(=O)N1CCC(N2CCCCC2)CC1]

4. The compound of claim 1, wherein $R^3$ is H.

5. The compound of claim 1, wherein $R^5$ is:

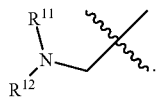

6. The compound of claim 1, wherein $R^{11}$ and $R^{12}$ independently is $C_1$-$C_8$ alkyl.

7. The compound of claim 6, wherein $R^{11}$ is methyl and $R^{12}$ is methyl.

8. The compound of claim 1, wherein $R^5$ is H.

9. The compound of claim 1, wherein $R^3$ is $C_1$-$C_8$ alkyl.

10. The compound of claim 1, wherein $R^3$ is an ethyl.

11. The compound of claim 1 selected from the group consisting of:

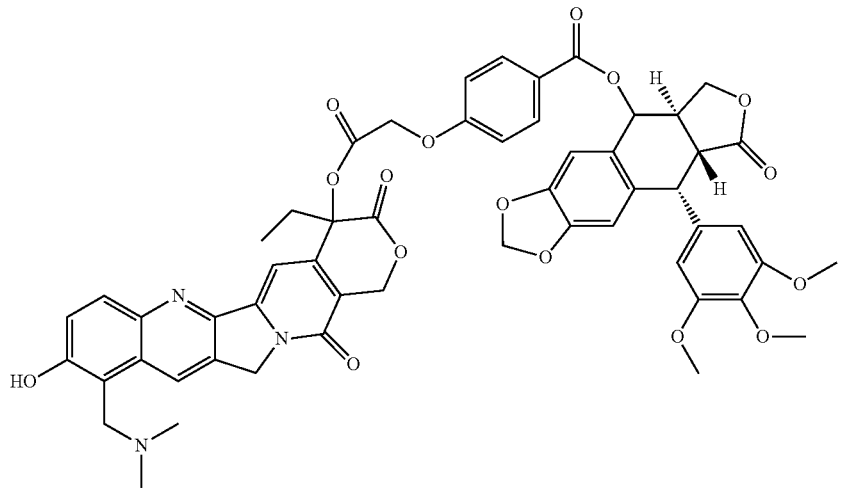

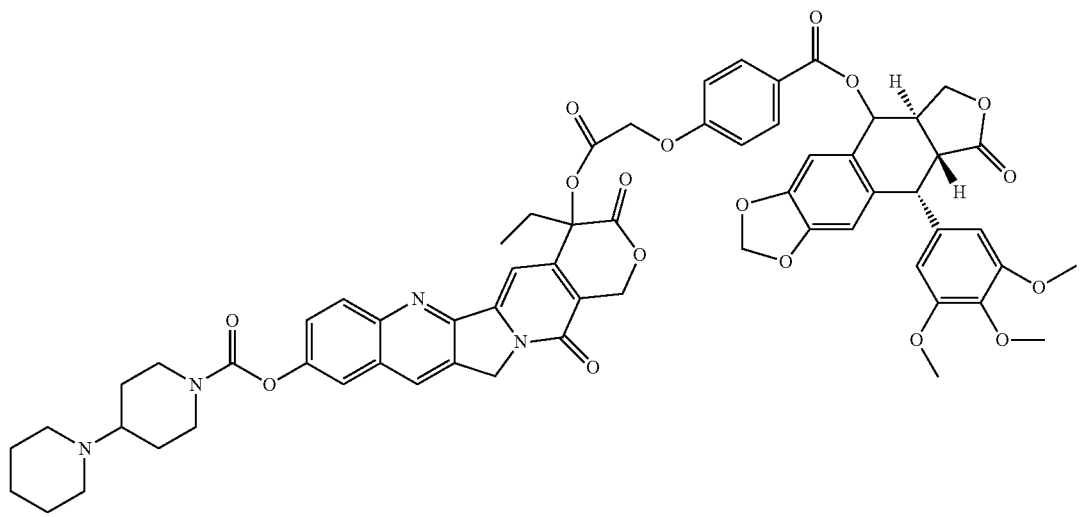

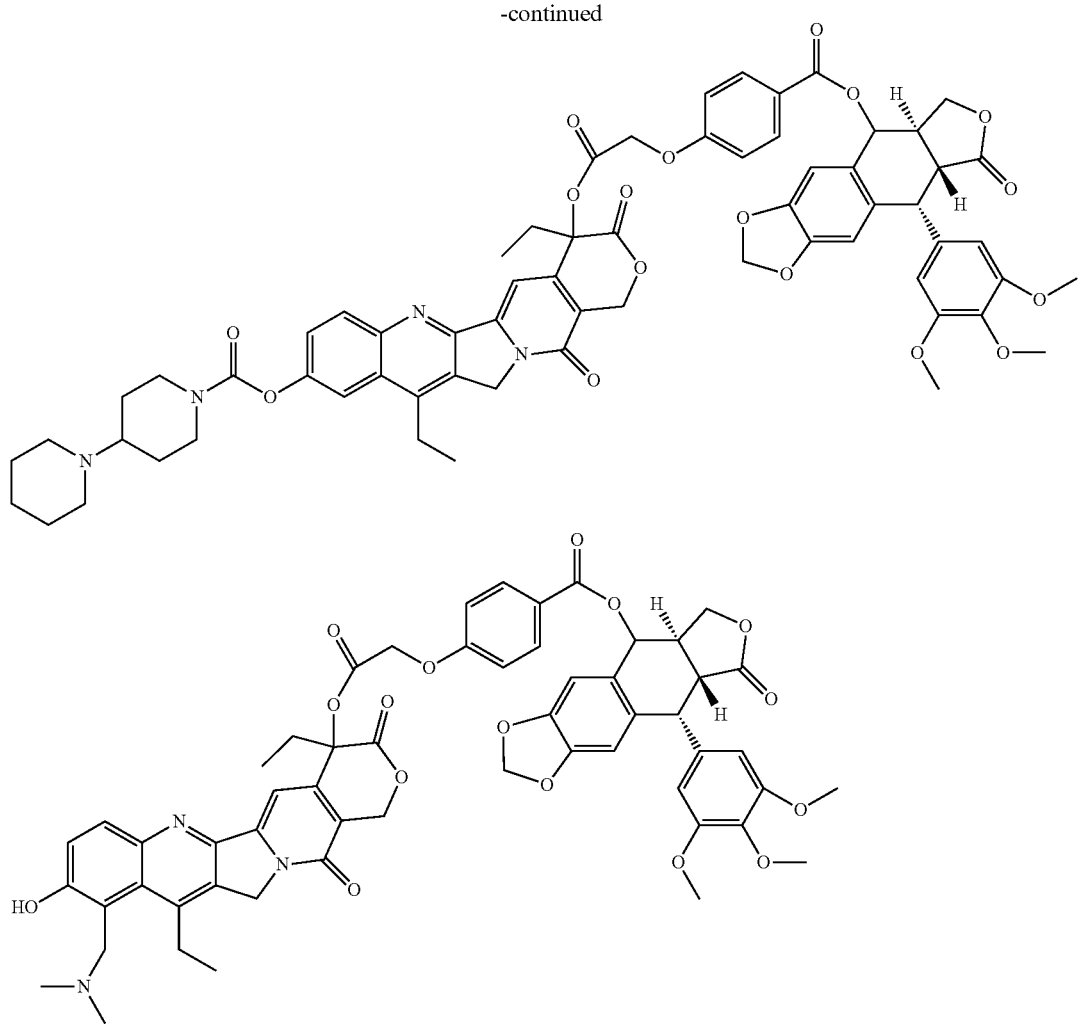

or an N-oxide thereof, or a pharmaceutically acceptable salt of each thereof, or a pharmaceutically acceptable solvate of each of the foregoing.

12. A pharmaceutical composition comprising a compound of claim 1 and at least one pharmaceutically acceptable excipient.

13. The pharmaceutical composition of claim 12, wherein the pharmaceutical composition is a solid form, liquid form, injectable form, or a liposomal formulation.

14. A pharmaceutical composition comprising a compound of claim 11 and at least one pharmaceutically acceptable excipient.

15. The pharmaceutical composition of claim 14, wherein the pharmaceutical composition is a solid form, liquid form, injectable form, or a liposomal formulation.

* * * * *

UNITED STATES PATENT AND TRADEMARK OFFICE
CERTIFICATE OF CORRECTION

PATENT NO. : 10,087,194 B2  
APPLICATION NO. : 14/924526  
DATED : October 2, 2018  
INVENTOR(S) : Li-Xi Yang It is certified that error appears in the above-identified patent and that said Letters Patent is hereby corrected as shown below:

In the Claims

In Claim 1, please replace the following chemical structure for compound of formula (I) in Column 46, Line 21:

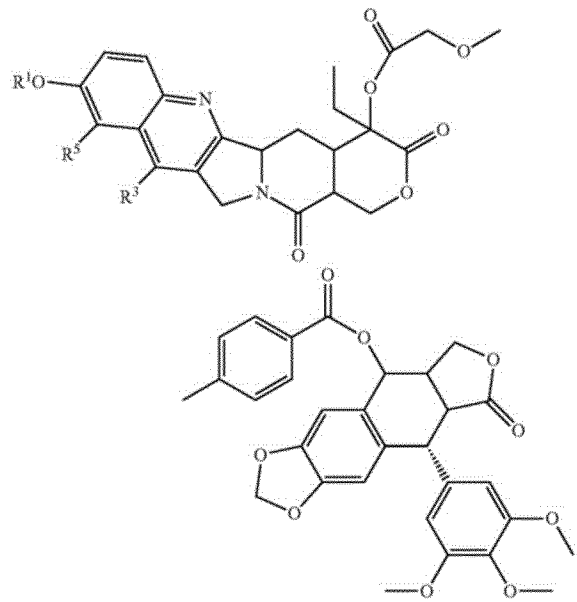

With:

Signed and Sealed this  
Fourteenth Day of April, 2020

Andrei Iancu  
*Director of the United States Patent and Trademark Office*